(12) United States Patent
Heaney

(10) Patent No.: US 11,419,845 B2
(45) Date of Patent: Aug. 23, 2022

(54) CANNABINOID DERIVATIVES AND METHODS FOR THEIR PREPARATION

(71) Applicant: John Heaney, Richland, WA (US)

(72) Inventor: John Heaney, Richland, WA (US)

( * ) Notice: Subject to any disclaimer, the term of this patent is extended or adjusted under 35 U.S.C. 154(b) by 40 days.

(21) Appl. No.: 16/704,194

(22) Filed: Dec. 5, 2019

(65) Prior Publication Data

US 2020/0179330 A1 Jun. 11, 2020

Related U.S. Application Data

(60) Provisional application No. 62/778,177, filed on Dec. 11, 2018.

(51) Int. Cl.
| | |
|---|---|
| *C07D 311/80* | (2006.01) |
| *C07C 33/26* | (2006.01) |
| *A61K 31/352* | (2006.01) |
| *A61K 31/05* | (2006.01) |
| *A61K 31/485* | (2006.01) |
| *A61K 31/60* | (2006.01) |
| *A61K 31/167* | (2006.01) |
| *A61K 31/192* | (2006.01) |
| *A61K 45/06* | (2006.01) |

(52) U.S. Cl.
CPC ............ *A61K 31/352* (2013.01); *A61K 31/05* (2013.01); *A61K 31/167* (2013.01); *A61K 31/192* (2013.01); *A61K 31/485* (2013.01); *A61K 31/60* (2013.01); *A61K 45/06* (2013.01); *C07C 33/26* (2013.01); *C07D 311/80* (2013.01)

(58) Field of Classification Search
CPC .............................. C07C 33/26; C07D 311/80
See application file for complete search history.

(56) References Cited

FOREIGN PATENT DOCUMENTS

| WO | WO-2012011112 A1 * | 1/2012 | ............. C07C 62/32 |
|---|---|---|---|
| WO | WO-2017008136 A3 * | 1/2017 | ............. A61P 25/24 |

* cited by examiner

*Primary Examiner* — Kevin E Weddington

(57) ABSTRACT

Novel compounds, pharmaceutical compositions containing these compounds, and methods for their pharmaceutical use are disclosed. In certain embodiments, the compounds are agonists and/or ligands of cannabinoid receptors and may be useful, inter alia, for treating and/or preventing pain, gastrointestinal disorders, genitourinary disorders, inflammation, glaucoma, auto-immune diseases, ischemic conditions, immune-related disorders, and neurodegenerative diseases, for providing cardioprotection against ischemic and reperfusion effects, for inducing apoptosis in malignant cells, and as an appetite stimulant.

9 Claims, No Drawings

CANNABINOID DERIVATIVES AND METHODS FOR THEIR PREPARATION

CROSS REFERENCE TO RELATED APPLICATIONS

This application claims the benefit of priority under 35 USC § 119(e) to U.S. Provisional Patent Application No. 62/778,177, titled "CANNABINOID DERIVATIVES AND METHODS FOR THEIR PREPARATION," filed on Dec. 11, 2018, the entire disclosure of which is hereby incorporated by reference for all purposes.

FIELD OF THE INVENTION

The disclosure generally relates to novel compounds and the use thereof. More particularly, the disclosure relates to novel cannabinoid analogs, derivatives and related compounds and their use, inter alia, as agonists of cannabinoid receptors.

BACKGROUND OF THE INVENTION

*Cannabis sativa* preparations have long been known as therapeutic agents to treat various diseases. The native active constituent, delta 9-tetrahydrocannabinol ($\Delta^9$-THC), is prescribed today, under the generic name dronabinol, as an anti-emetic and for enhancement of appetite, mainly in AIDS patients. However, separation between the clinically undesirable psychotropic effects and the therapeutically desirable effects on the peripheral nervous systems, the cardiovascular system, and the immune and endocrine systems is problematic.

Cannabidiol (CBD) is a naturally occurring cannabinoid constituent of *cannabis*. It was discovered in 1940 and initially thought not to be pharmaceutically active. It is one of at least 113 cannabinoids identified in hemp plants, accounting for up to 40% of the plant's extract.

The discovery of two cannabinoid receptors, CB1 and CB2, has helped to elucidate the diverse cannabinoid effects. The CB1 receptor has been cloned from rat, mouse, and human tissues and exhibits 97-99% amino acid sequence identity across species. The CB2 receptor exhibits 48% homology with the CB1 receptor. The structures of both receptors are consistent with seven transmembrane G-protein coupled receptors. In addition, both receptors exert their effect by negative regulation of adenylyl cyclase activity through pertussis toxin-sensitive GTP-binding proteins. They were also shown to activate the mitogen activated protein kinase (MAPK) in certain cell types.

The CB1 receptor is expressed mainly in the central nervous system (CNS) and to a lesser extent in other tissues including, for example, gastrointestinal tissues, immune cells, reproductive organs, heart, lung, urinary bladder and adrenal gland. The CB2 receptor is expressed mostly in peripheral tissue associated with immune functions including, for example, macrophages, B, T cells and mast cells, as well as in peripheral nerve terminals. The central distribution pattern of CB1 receptors accounts for several unwanted pharmacological properties of cannabinoid, such as impaired cognition and memory, altered control of motor function, and psychotropic and other neurobehavioral effects. CB1 receptors are also found on pain pathways in brain, spinal cord and at the peripheral terminals of primary sensory neurons. CB2 receptors have not been observed within the CNS.

CB1 knockout mice have been shown to be unresponsive to cannabinoids in behavioral assays providing molecular evidence that the psychotropic effects, including sedation, hallucinations and antinociception are manifested through the activation of the CB1 receptor that are present primarily in the CNS. Analysis of the CB2 knockout mouse has corroborated the evidence for the function of CB2 receptors in modulating the immune system. The CB2 receptor does not affect immune cell development and differentiation as determined by FACS analysis of cells from the spleen, lymph node and thymus from CB2 knockout mice. Further studies in these mice have shown that the immunosuppressive effects of $\Delta^9$-THC are mediated by the CB2 receptor.

Cannabinoid receptor agonists, such as CP55,940 and WIN 55,212-2, produce potent antinociception with equivalent efficacy to morphine in animal models of acute pain, persistent inflammatory pain, and neuropathic pain. They also induce a number of unwanted CNS side effects. Furthermore, the known cannabinoid receptor agonists are in general highly lipophilic and insoluble in water. Thus, there is a need for cannabinoid receptor agonists with improved properties for the use as therapeutic agents.

SUMMARY OF THE INVENTION

Accordingly, the disclosure is directed, in part, to novel compounds, which may be agonists of cannabinoid receptors, which may be useful, inter alia, for the treatment of diseases or disorders which are associated with the cannabinoid receptor system. The disclosed cannabinoid compounds and compositions have unique medicinal properties, both alone and in combination with other cannabinoids. The disclosed compounds bear similarities to a number of the minor cannabinoids and have similar toxicities, i.e., virtually zero toxicity. The disclosed compounds and compositions show strong anti-inflammatory action, along with mild analgesia; in combination with micro-doses of THC, they demonstrate analgesia equivalent to morphine without tolerance, addiction, withdrawal or mental/physical impairment, or noticeable side effects (post-surgical healing time appears to be cut in half or less). The disclosed compounds and compositions provide all the benefits that CBD and other cannabinoids have promised but are unable to deliver.

The disclosed compounds and compositions, at low doses, block the metabolism of THC, preventing formation of 11-Hydroxy THC, which is responsible for most of the negative effects attributed to THC, e.g., mental and physical impairment, drowsiness, lassitude, paranoia, red eyes and uncontrolled hunger. This allows small doses of THC to exert full medical benefit without the undesirable side-effects. Alone the compounds and compositions mimic the actions of the minor cannabinoids, but with greatly-enhanced activity.

Thus, in one embodiment, the disclosure relates to compounds of Formula I:

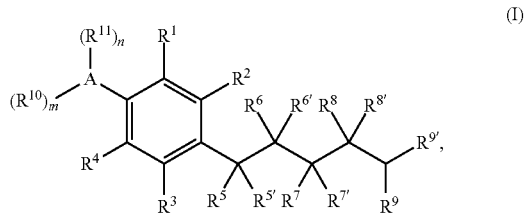

or a pharmaceutically acceptable salt thereof, wherein:

$R^1$, $R^2$, $R^3$ and $R^4$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)R$^{12}$, —NHC(=O)R$^{12}$, —N(R$^{13}$)(R$^{14}$), —C(=O)N(R$^{13}$)(R$^{14}$), —OC(=O)N(R$^{13}$)(R$^{14}$), —NHC(=O)N(R$^{13}$)(R$^{14}$), and —C(=O)CHR$^{15}$N(R$^{13}$)(R$^{14}$), each of which group may optionally be unsubstituted or substituted with one or more substituents, or $R^1$ and $R^2$, and/or $R^2$ and $R^5$, and/or $R^2$ and $R^6$, and/or $R^2$ and $R^7$, taken together with the carbon atoms to which each are attached, independently form a 4- to 8-membered ring, wherein 1 or 2 of the ring atoms independently are optionally replaced by —O—, —(C(=O)—, —(C(=O)O—, —NH—, —N(C$_1$-C$_6$)alkyl)-, —(C(=O)NH—, or —(C(=O)N(C$_1$-C$_6$)alkyl)-, and $R^3$ and $R^4$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)OR$^{12}$, —NHC(=O)R$^{12}$, —N(R$^{13}$)(R$^{14}$), —C(=O)N(R$^{13}$)(R$^{14}$), —OC(=O)N(R$^{13}$)(R$^{14}$), —NHC(=O)N(R$^{13}$)(R$^{14}$), and —C(=O)CHR$^{15}$N(R$^{13}$)(R$^{14}$), each of which group may optionally be unsubstituted or substituted with one or more substituents;

$R^5$, $R^{5'}$, $R^6$, $R^{6'}$, $R^7$, $R^{7'}$, $R^8$, $R^{8'}$, $R^9$, and $R^{9'}$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)OR$^{12}$, —NHC(=O)R$^{12}$, —N(R$^{13}$)(R$^{14}$), —C(=O)N(R$^{13}$)(R$^{14}$), —OC(=O)N(R$^{13}$)(R$^{14}$), —NHC(=O)N(R$^{13}$)(R$^{14}$), and —C(=O)CHR$^{15}$N(R$^{13}$)(R$^{14}$), each of which group may optionally be unsubstituted or substituted with one or more substituents, or $R^5$, $R^{5'}$, and/or $R^6$, $R^{6'}$, and/or $R^7$, $R^{7'}$, and/or $R^8$, $R^{8'}$, and/or $R^9$, and $R^{9'}$ each independently form C=O, C=S, or C=NH, or $R^5$ and $R^6$, or $R^5$ and $R^7$, or $R^6$ and $R^7$, or $R^6$ and $R^8$, or $R^7$ and $R^8$, or $R^7$ and $R^9$, or $R^8$ and $R^9$ taken together with the carbon atoms to which each are attached, independently form a 4- to 8-membered ring, wherein 1 or 2 of the ring atoms independently are optionally replaced by —O—, —(C(=O)—, —(C(=O)O—, —NH—, —N(C$_1$-C$_6$)alkyl)-, —(C(=O)NH—, or —(C(=O)N(C$_1$-C$_6$)alkyl)-, and the remainder of $R^5$ and $R^6$, or $R^5$ and $R^7$, or $R^6$ and $R^7$, or $R^6$ and $R^8$, or $R^7$ and $R^8$, or $R^7$ and $R^9$, or $R^8$ and $R^9$, are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —C(=O)R$^{12}$, —C(=O)OR$^{12}$, —OC(=O)R$^{12}$, —OC(=O)OR$^{12}$, —NHC(=O)R$^{12}$, —N(R$^{13}$)(R$^{14}$), —C(=O)N(R$^{13}$)(R$^{14}$), —NHC(=O)N(R$^{13}$)(R$^{14}$), and —C(=O)CHR$^{15}$N(R$^{13}$)(R$^{14}$), each of which group may optionally be unsubstituted or substituted with one or more substituents;

A is independently selected from alkyl, alkenyl, alkynyl, cycloalkyl, cycloalkenyl, heterocycloalkyl, alkoxy, aryl, aralkyl, heteroaryl, heteroaralkyl, 5- or 6-membered heterocyclic ring, 5- or 6-membered heteroaryl ring, and a 6-membered aryl ring, each of which group may be optionally unsubstituted or substituted with one or more substituents;

$R^{10}$ and $R^{11}$ are each independently selected from hydrogen, hydroxyl, halogen, alkyl, alkenyl, alkynyl, cycloalkyl, spiroalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)OR$^{12}$, —NHC(=O)R$^{12}$, —N(R$^{13}$)(R$^{14}$), —C(=O)N(R$^{13}$)(R$^{14}$), —OC(=O)N(R$^{13}$)(R$^{14}$), —NHC(=O)N(R$^{13}$)(R$^{14}$), and —C(=O)CHR$^{15}$N(R$^{13}$)(R$^{14}$), each of which group may optionally be unsubstituted or substituted with one or more substituents, or $R^{10}$ and $R^{11}$, taken together with the atom to which they are attached, independently form a substituted or unsubstituted 4 to 8 membered cyclic or heterocyclic ring, or a 5 membered heteroaryl ring, or a 6 membered aryl ring;

m and n are each independently an integer ranging from 0 to 5;

$R^{12}$ is each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —N(R$^{13}$)(R$^{14}$), —C(=O)N(R$^{13}$)(R$^{14}$), —OC(=O)N(R$^{13}$)(R$^{14}$), —NHC(=O)N(R$^{13}$)(R$^{14}$), and —C(=O)CHR$^{15}$N(R$^{13}$)(R$^{14}$), each of which group may optionally be unsubstituted or substituted with one or more substituents;

$R^{13}$ and $R^{14}$ are each independently selected from hydrogen, alkyl, alkenyl, alkynyl, cycloalkyl, cycloalkenyl, heterocycloalkyl, aryl, aralkyl, heteroaryl, and heteroaralkyl, or $R^{13}$ and $R^{14}$, taken together with the nitrogen atom to which they are attached, independently form a 4- to 8-membered heterocyclic ring wherein 1 or 2 of the ring atoms independently are optionally replaced by —O—, —S—, —S(=O)—, —S(=O)$_2$—, —NH—, —N(alkyl)-, —N(C(=O)R$^{12}$)—, or —N(S(=O)$_2$—R$^{12}$)—; and $R^{15}$ is independently selected from hydrogen, alkyl, alkenyl, alkynyl, cycloalkyl, cycloalkenyl, heterocycloalkyl, aryl, aralkyl, heteroaryl, and heteroaralkyl.

In another embodiment, the disclosure relates to compounds of Formula I, wherein A has formula:

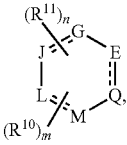

wherein Q, E, G, J, L, and M are each independently selected from —C—, —CH—, —CR10-, —CR11-, —C=, —N—, —NH—, —NR10- —NR11-, —O—, and —S—, or one of Q, E, G, J, L, and M is and absent, and the other of Q, E, G, J, L, and M are each independently selected from —C—, —CH—, —CR10-, —CR11-, —C=, —N—, —NR10- —NR11-, —N=, —O—, and —S—.

In another embodiment, the disclosure relates to compounds of Formula I, wherein $R^1$ and $R^4$ are each independently selected from hydrogen, —OR$^{12}$, and —N(R$^{13}$)(R$^{14}$).

In another embodiment, the disclosure relates to compounds of Formula I, wherein $R^1$ and $R^4$ are each independently selected from hydrogen, —OH, —O(C$_1$-C$_6$)alkyl, —NH(C$_1$-C$_6$)alkyl, and —N[(C$_1$-C$_6$)alkyl]$_2$.

In another embodiment, the disclosure relates to compounds of Formula I, wherein $R^2$ and $R^3$ are each independently selected from hydrogen, alkyl, —C(=O)R$^{12}$, —C(=O)OR$^{12}$, —CN, —C(=O)N(R$^{13}$)(R$^{14}$), and —C(=O)CHR$^{15}$N(R$^{13}$)(R$^{14}$).

In another embodiment, the disclosure relates to compounds of Formula I, wherein $R^2$ and $R^3$ are each independently selected from hydrogen, —(C$_1$-C$_6$)alkyl, —C(=O)(C$_1$-C$_6$)alkyl, —C(=O)O(C$_1$-C$_6$)alkyl, —CN, —C(=O)

NH($C_1$-$C_6$)alkyl, —C(=O)N[($C_1$-$C_6$)alkyl]$_2$, —C(=O)CHR$^{15}$NH($C_1$-$C_6$)alkyl, and —C(=O)CHR$^{15}$N[($C_1$-$C_6$)alkyl]$_2$.

In another embodiment, the disclosure relates to compounds of Formula I, wherein R$^1$ and R$^4$ are each independently selected from —OH and —O($C_1$-$C_6$)alkyl; and R$^2$ and R$^3$ are each independently selected from hydrogen and —C(=O)($C_1$-$C_6$)alkyl.

In another embodiment, the disclosure relates to compounds of Formula I, wherein R$^5$, R$^{5'}$, R$^6$, R$^{6'}$, R$^7$, R$^{7'}$, R$^8$, R$^{8'}$, R$^9$, and R$^{9'}$ are each independently selected from hydrogen, —($C_1$-$C_6$)alkyl, F, Cl, Br, I, —OH, and —O($C_1$-$C_6$)alkyl.

In another embodiment, the disclosure relates to compounds of Formula I, wherein R$^{10}$ and R$^{11}$ are each independently selected from hydrogen and —($C_1$-$C_6$)alkyl.

In another embodiment, the disclosure relates to compounds of Formula I, wherein R$^{10}$ and R$^{11}$ are each independently selected from hydrogen, —CH$_3$, —CH$_2$CH$_3$, —CH=CH$_2$, —CH$_2$CH$_2$CH$_3$, —CH=CCH$_3$, —CH$_2$CH=CH$_2$, —C=CHCH$_2$CH$_3$, —CH$_2$CH=CHCH$_3$, —CH$_2$CH$_2$CH=CH, —CH$_2$CH(CH$_3$)$_2$, —CH=C(CH$_3$)$_2$, —CH$_2$C(=CH$_2$)(CH$_3$), —CH(CH$_3$)CH$_2$CH$_3$, —C(=CH$_2$)CH$_2$CH$_3$, and —CH(CH$_3$)C=CH$_2$.

In another embodiment, the disclosure relates a pharmaceutical composition, comprising a pharmaceutically acceptable carrier and one or more compounds of Formula I.

In another embodiment, the disclosure relates a pharmaceutical composition, comprising a pharmaceutically acceptable carrier and one or more compounds of Formula I, further comprising at least one cannabinoid.

In another embodiment, the disclosure relates a pharmaceutical composition, comprising a pharmaceutically acceptable carrier and one or more compounds of Formula I, further comprising at least one cannabinoid wherein the cannabinoid is Δ$^9$-tetrahydrocannabinol or cannabidiol.

In another embodiment, the disclosure relates a pharmaceutical composition, comprising a pharmaceutically acceptable carrier and one or more compounds of Formula I, further comprising at least one opioid.

In another embodiment, the disclosure relates a pharmaceutical composition, comprising a pharmaceutically acceptable carrier and one or more compounds of Formula I, further comprising at least one opioid, wherein the at least one opioid is selected from alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil, tramadol, and mixtures thereof.

In another embodiment, the disclosure relates a pharmaceutical composition, comprising a pharmaceutically acceptable carrier and one or more compounds of Formula I, further comprising at least one analgesic.

In another embodiment, the disclosure relates a pharmaceutical composition, comprising a pharmaceutically acceptable carrier and one or more compounds of Formula I, further comprising at least one analgesic, wherein the analgesic is selected from a COX2 inhibitor, aspirin, acetaminophen, ibuprofen, naproxen, and mixtures thereof.

In another embodiment, the disclosure relates a pharmaceutical composition, comprising a pharmaceutically acceptable carrier and one or more compounds of Formula I, further comprising at least one agent selected from an anti-seizure agent, an anti-depressant, an NMDA receptor antagonist, an ion channel antagonist, a nicotinic receptor agonist, an anti-Parkinson's agent, and mixtures thereof.

In another embodiment, the disclosure relates a pharmaceutical composition, comprising a pharmaceutically acceptable carrier and one or more compounds of Formula I, further comprising at least one agent selected from an anti-seizure agent, an anti-depressant, an NMDA receptor antagonist, an ion channel antagonist, a nicotinic receptor agonist, an anti-Parkinson's agent, and mixtures thereof, wherein the anti-seizure agent is selected from carbamazepine, gabapentin, lamotrigine, phenytoin, and mixtures thereof; the anti-depressant is amitriptyline; and the anti-Parkinson's agent is selected from deprenyl, amantadine, levodopa, or carbidopa, and mixtures thereof.

In another embodiment, the disclosure relates a method of preparing one or more compounds of Formula I:

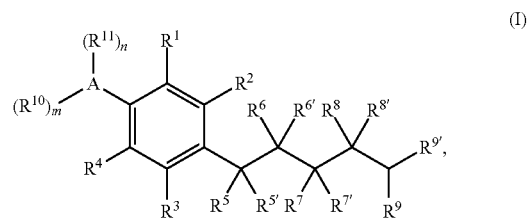

or a pharmaceutically acceptable salt thereof, comprising:
a) reacting a compound of Formula II with an acylation reagent to provide the compound of Formula I:

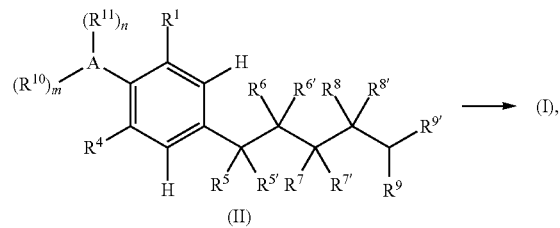

wherein:
R$^1$, R$^2$, R$^3$ and R$^4$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)OR$^{12}$, —NHC(=O)R$^{12}$, —N(R$^{13}$)(R$^{14}$), —C(=O)N(R$^{13}$)(R$^{14}$), —OC(=O)N(R$^{13}$)(R$^{14}$), —NHC(=O)N(R$^{13}$)(R$^{14}$), and —C(=O)CHR$^{15}$N(R$^{13}$)(R$^{m}$), each of which group may optionally be unsubstituted or substituted with one or more substituents, or R$^1$ and R$^2$, and/or R$^2$ and R$^5$, and/or R$^2$ and R$^6$, and/or R$^2$ and R$^7$, taken together with the carbon atoms to which each are attached, independently form a 4- to 8-membered ring, wherein 1 or 2 of the ring atoms independently are optionally replaced by —O—, —(C(=O)—, —(C(=O)O—, —NH—, —N($C_1$-$C_6$)alkyl)-, —(C(=O)NH—, or —(C(=O)N($C_1$-$C_6$)alkyl)-, and R$^3$ and R$^4$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)OR$^{12}$, —NHC(=O)R$^{12}$, —N(R$^{13}$)(R$^{14}$), —C(=O)N(R$^{13}$)(R$^{14}$), —OC(=O)N(R$^{13}$)(R$^{14}$), —NHC (=O)N($R^{13}$)($R^{14}$), and —C(=O)CH$R^{15}$N($R^{13}$)($R^{14}$), each of which group may optionally be unsubstituted or substituted with one or more substituents;

$R^5$, $R^{5'}$, $R^6$, $R^{6'}$, $R^7$, $R^{7'}$, $R^8$, $R^{8'}$, $R^9$, and $R^{9'}$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —O$R^{12}$, —C(=O)$R^{12}$, —C(=O)O$R^{12}$, —OC(=O)$R^{12}$, —OC(=O)O$R^{12}$, —NHC(=O)$R^{12}$, —N($R^{13}$)($R^{14}$), —C(=O)N($R^{13}$)($R^{14}$), —OC(=O)N($R^{13}$)($R^{14}$), —NHC(=O)N($R^{13}$)($R^{14}$), and —C(=O)CH$R^{15}$N($R^{13}$)($R^{14}$), each of which group may optionally be unsubstituted or substituted with one or more substituents, or $R^5$, $R^{5'}$, and/or $R^6$, $R^{6'}$, and/or $R^7$, $R^{7'}$, and/or $R^8$, $R^{8'}$, and/or $R^9$, and $R^{9'}$ each independently form C=O, C=S, or C=NH, or $R^5$ and $R^6$, or $R^5$ and $R^7$, or $R^6$ and $R^7$, or $R^6$ and $R^8$, or $R^7$ and $R^8$, or $R^7$ and $R^9$, or $R^8$ and $R^9$ taken together with the carbon atoms to which each are attached, independently form a 4- to 8-membered ring, wherein 1 or 2 of the ring atoms independently are optionally replaced by —O—, —(C(=O)—, —(C(=O)O—, —NH—, —N($C_1$-$C_6$)alkyl)-, —(C(=O)NH—, or —(C(=O)N($C_1$-$C_6$)alkyl)-, and the remainder of $R^5$ and $R^6$, or $R^5$ and $R^7$, or $R^6$ and $R^7$, or $R^6$ and $R^8$, or $R^7$ and $R^8$, or $R^7$ and $R^9$, or $R^8$ and $R^9$, are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —O$R^{12}$, —C(=O)$R^{12}$, —C(=O)O$R^{12}$, —OC(=O)$R^{12}$, —OC(=O)O$R^{12}$, —NHC(=O)$R^{12}$, —N($R^{13}$)($R^{14}$), —C(=O)N($R^{13}$)($R^{14}$), —OC(=O)N($R^{13}$)($R^{14}$), —NHC(=O)N($R^{13}$)($R^{14}$), and —C(=O)CH$R^{15}$N($R^{13}$)($R^{14}$), each of which group may optionally be unsubstituted or substituted with one or more substituents;

A is independently selected from alkyl, alkenyl, alkynyl, cycloalkyl, cycloalkenyl, heterocycloalkyl, alkoxy, aryl, aralkyl, heteroaryl, heteroaralkyl, 5- or 6-membered heterocyclic ring, 5- or 6-membered heteroaryl ring, and a 6-membered aryl ring, each of which group may be optionally unsubstituted or substituted with one or more substituents;

$R^{10}$ and $R^{11}$ are each independently selected from hydrogen, hydroxyl, halogen, alkyl, alkenyl, alkynyl, cycloalkyl, spiroalkyl, cycloalkenyl, heterocycloalkyl, alkoxy, aryl, aralkyl, heteroaryl, heteroaralkyl, nitro, cyano, —O$R^{12}$, —C(=O)$R^{12}$, —C(=O)O$R^{12}$, —OC(=O)$R^{12}$, —OC(=O)O$R^{12}$, —NHC(=O)$R^{12}$, —N($R^{13}$)($R^{14}$), —C(=O)N($R^{13}$)($R^{14}$), —OC(=O)N($R^{13}$)($R^{14}$), —NHC(=O)N($R^{13}$)($R^{14}$), and —C(=O)CH$R^{15}$N($R^{13}$)($R^{14}$), each of which group may optionally be unsubstituted or substituted with one or more substituents, or $R^{10}$ and $R^{11}$, taken together with the atom to which they are attached, independently form a substituted or unsubstituted 4 to 8 membered cyclic or heterocyclic ring, or a 5 membered heteroaryl ring, or a 6 membered aryl ring;

m and n are each independently an integer ranging from 0 to 5;

$R^{12}$ is each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —N($R^{13}$)($R^{14}$), —C(=O)N($R^{13}$)($R^{14}$), —OC(=O)N($R^{13}$)($R^{14}$), —NHC(=O)N($R^{13}$)($R^{14}$), and —C(=O)CH$R^{15}$N($R^{13}$)($R^{14}$), each of which group may optionally be unsubstituted or substituted with one or more substituents;

$R^{13}$ and $R^{14}$ are each independently selected from hydrogen, alkyl, alkenyl, alkynyl, cycloalkyl, cycloalkenyl, heterocycloalkyl, aryl, aralkyl, heteroaryl, and heteroaralkyl, or $R^{13}$ and $R^{14}$, taken together with the nitrogen atom to which they are attached, independently form a 4- to 8-membered heterocyclic ring wherein 1 or 2 of the ring atoms independently are optionally replaced by —O—, —S—, —S(=O)—, —S(=O)$_2$—, —NH—, —N(alkyl)-, —N(C(=O)$R^{12}$)—, or —N(S(=O)$_2$—$R^{12}$)—; and $R^{15}$ is independently selected from hydrogen, alkyl, alkenyl, alkynyl, cycloalkyl, cycloalkenyl, heterocycloalkyl, aryl, aralkyl, heteroaryl, and heteroaralkyl.

In another embodiment, the disclosure relates a method of preparing a compound of Formula I, or a pharmaceutically acceptable salt thereof, comprising: a) reacting a compound of Formula II with an acylation reagent to provide the compound of Formula I, wherein the acylation reagent is an anhydride or an acid halide or pseudohalide.

In yet another embodiment, the disclosure is also directed, in part, to methods for binding cannabinoid receptors in a patient in need thereof, by administering to a patient an effective amount of at least one compound of Formula I. In one form, the disclosed cannabinoid receptor agonists may be used in methods for the treatment or prevention of a disease or disorder selected from pain, gastrointestinal disorders, genitourinary disorders, inflammation, glaucoma, auto-immune diseases, ischemic conditions, immune-related disorders, and neurodegenerative diseases, and combinations thereof. In alternate embodiments, the disclosed compounds and compositions can be used in the methods for providing cardioprotection against ischemic and reperfusion effects, for inducing apoptosis in malignant cells, and for appetite modulation.

These and other aspects of the disclosure will become more apparent from the specification and claims.

DETAILED DESCRIPTION OF THE EMBODIMENTS

The disclosure is generally directed to compounds, their use, inter alia, as agonists of cannabinoid receptors, pharmaceutical compositions containing these compounds, and methods of their pharmaceutical use.

As employed above and throughout the disclosure, the following terms, unless otherwise indicated, shall be understood to have the following meanings.

As used herein, "alkyl" refers to an optionally substituted, saturated straight, or branched, hydrocarbon radical having from about 1 to about 20 carbon atoms (and all combinations and subcombinations of ranges and specific numbers of carbon atoms therein). Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

As used herein, "perfluoroalkyl" refers to an optionally substituted alkyl group from about 1 to about 20 carbon atoms (and all combinations and subcombinations of ranges and specific numbers of carbon atoms therein), wherein the carbon atoms are substituted with fluorine.

As used herein, "alkenyl" refers to an optionally substituted alkyl group having from about 2 to about 10 carbon atoms and one or more double bonds (and all combinations and subcombinations of ranges and specific numbers of carbon atoms therein), wherein alkyl is as previously defined.

As used herein, "acyl" refers to an alkyl-C(=O)— group, wherein alkyl is as previously defined.

As used herein, "alkylene" refers to an optionally substituted bivalent alkyl radical having the general formula —(CH$_2$)$_n$—, where n is 1 to 10. Non-limiting examples include methylene, dimethylene, trimethylene, pentamethylene, and hexamethylene.

As used herein, "alkylidene" refers to an optionally substituted bivalent aliphatic radical derived from univalent aliphatic or cycloaliphatic hydrocarbon radicals whose names end in "yl" by removal of one of the hydrogen atoms from the carbon atom with the free valence, said radical having from about 1 to about 20 carbon atoms (and all combinations and subcombinations of ranges and specific numbers of carbon atoms therein).

As used herein, "lower alkylidene" refers to those divalent aliphatic and cycloaliphatic groups with from about 1 to about 10 carbon atoms. Alkylidene groups include, but are not limited to, methylidene, ethylidene, n-propylidene, iso-propylidene, cyclopropylidene, n-butylidene, isobutylidene, t-butylidene, 2-butenylidene, 2-butynylidene, n-pentylidene, cyclopentylidene, isopentylidene, neopentylidene, n-hexylidene, isohexylidene, cyclohexylidene, cyclooctylidene, adamantylidene, 3-methylidene pentylidene, 2,2-dimethylidene butylidene, and 2,3-dimethylbutylidene.

As used herein, "alkynyl" refers to an optionally substituted alkyl group having from about 2 to about 10 carbon atoms and one or more triple bonds (and all combinations and subcombinations of ranges and specific numbers of carbon atoms therein), wherein alkyl is as previously defined.

As used herein, "alkoxy" and "alkoxyl" refer to an optionally substituted alkyl-O-group wherein alkyl is as previously defined. Exemplary alkoxy and alkoxyl groups include methoxy, ethoxy, n-propoxy, i-propoxy, n-butoxy, and heptoxy.

As used herein, "aryl" and "aromatic" each refer to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being included. Non-limiting examples include, for example, phenyl, naphthyl, anthracenyl, and phenanthrenyl.

As used herein, "aralkyl" refers to an optionally substituted moiety composed of an alkyl radical bearing an aryl substituent and having from about 6 to about 50 carbon atoms (and all combinations and subcombinations of ranges and specific numbers of carbon atoms therein), with from about 6 to about 10 carbon atoms being included. Non-limiting examples include, for example, benzyl, diphenylmethyl, triphenylmethyl, phenylethyl, and diphenylethyl.

As used herein, "heteroaryl" refers to an optionally substituted aryl ring system wherein in at least one of the rings, one or more of the carbon atom ring members is independently replaced by a heteroatom group selected from the group consisting of S, O, N, and NH, wherein aryl is as previously defined. Heteroaryl groups having a total of from about 5 to about 14 carbon atom ring members and heteroatom ring members (and all combinations and subcombinations of ranges and specific numbers of carbon and heteroatom ring members) are included. Exemplary heteroaryl groups include, but are not limited to, pyrryl, furyl, pyridyl, pyridine-N-oxide, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be attached via a carbon or a heteroatom to the rest of the molecule.

As used herein, "cycloalkyl" or "carbocyclic ring" each refers to an optionally substituted, mono-, di-, tri-, or other multicyclic alicyclic ring system having from about 3 to about 20 carbon atoms (and all combinations and subcombinations of ranges and specific numbers of carbon atoms therein). In some embodiments, the cycloalkyl groups have from about 3 to about 8 carbon atoms. Multi-ring structures may be bridged or fused ring structures, wherein the additional groups fused or bridged to the cycloalkyl ring may include optionally substituted cycloalkyl, aryl, heterocycloalkyl, or heteroaryl rings. Exemplary cycloalkyl groups include, but are not limited to, cyclopropyl, cyclobutyl, cyclopentyl, cyclohexyl, cyclooctyl, adamantyl, 2-[4-isopropyl-1-methyl-7-oxa-bicyclo[2.2.1]heptanyl], and 2-[1,2,3,4-tetrahydro-naphthalenyl].

As used herein, "alkylcycloalkyl" refers to an optionally substituted ring system comprising a cycloalkyl group having one or more alkyl substituents, wherein cycloalkyl and alkyl are each as previously defined. Exemplary alkylcycloalkyl groups include, for example, 2-methylcyclohexyl, 3,3-dimethylcyclopentyl, trans-2,3-dimethylcyclooctyl, and 4-methyldecahydronaphthalenyl.

As used herein, a "cannabinoid" compound includes a group of closely related compounds that include cannabinol and the active constituents of *cannabis*. As used herein, a "cannabinoid" compound also includes a "cannabimimetic" compound.

As used herein, a "cannabimimetic" compound includes compounds having similar pharmacological effects to those of *cannabis* as applied to various cannabinoid receptor type 1 agonists. As used herein, "cannabimimetic" refers to any of a group of endogenous or exogenous receptor ligands that bind one or more of the receptors bound by cannabinoids and mimic one or more behaviors of cannabinoids while so bound. Examples of endogenous cannabimimetics (also referred to as "endocannabinoids") produced in mammalian tissues include, for example, arachidonoylethanolamide (anandamide), 2-arachidonoyl glycerol, 1(3)-arachidonoyl glycerol, and palmitoylethanolamide. Examples of exogenous cannabimimetics include, for example WIN 55,212-2, CP 55,940, HU-210, and the like. Other examples of exogenous cannbimimetics may be found in publications such as R. B. Pertwee, "Pharmacology of Cannabinoid Receptor Ligands", Current Medicinal Chemistry, 1999, 6, 635-664, and A. C. Howlett, et al. "International Union of Pharmacology. XXVII. Classification of Cannabinoid Receptors", Pharmacological Reviews, 2002, 54(2), 161-202, the disclosures of which are each hereby incorporated herein by reference, in their entireties.

As used herein, "cycloalkylalkyl" refers to an optionally substituted ring comprising an alkyl radical having one or more cycloalkyl substituents, wherein cycloalkyl and alkyl are as previously defined. In some embodiments, the alkyl moieties of the cycloalkylalkyl groups have from about 1 to about 3 carbon atoms. Exemplary cycloalkylalkyl groups include, but are not limited to, cyclohexylmethyl, 4-[4-methyldecahydronaphthalenyl]-pentyl, 3-[trans-2,3-dimethylcyclooctyl]-propyl, and cyclopentylethyl.

As used herein, "heteroaralkyl" and "heteroarylalkyl" each refers to an optionally substituted ring system comprising an alkyl radical bearing a heteroaryl substituent, having from about 2 to about 50 carbon atoms (and all combinations and subcombinations of ranges and specific numbers of carbon atoms therein), with from about 6 to about 25 carbon atoms being included. Non-limiting examples include 2-(1H-pyrrol-3-yl)ethyl, 3-pyridylmethyl, 5-(2H-tetrazolyl)methyl, and 3-(pyrimidin-2-yl)-2-methyl-cyclopentanyl.

As used herein, "heterocycloalkyl" and "heterocyclic ring" each refers to an optionally substituted ring system composed of a cycloalkyl radical wherein in at least one of the rings, one or more of the carbon atom ring members is independently replaced by a heteroatom group selected from the group consisting of O, S, N, NR, and NH, wherein cycloalkyl is as previously defined. Heterocycloalkyl ring systems having a total of from about 5 to about 14 carbon atom ring members and heteroatom ring members (and all combinations and subcombinations of ranges and specific numbers of carbon and heteroatom ring members) are included. In other embodiments, the heterocyclic groups may be fused to one or more aromatic rings. Heterocycloalkyl may be attached via a ring carbon or a ring heteroatom to the rest of the molecule. Exemplary heterocycloalkyl groups include, but are not limited to, azepanyl, tetrahydrofuranyl, hexahydropyrimidinyl, tetrahydrothienyl, piperidinyl, pyrrolidinyl, isoxazolidinyl, isothiazolidinyl, pyrazolidinyl, oxazolidinyl, thiazolidinyl, piperazinyl, 2-oxomorpholinyl, morpholinyl, 2-oxo-piperidinyl, piperadinyl, decahydroquinolyl, octahydrochromenyl, octahydro-cyclopenta[c]pyranyl, 1,2,3,4,-tetrahydroquinolyl, 1,2,3,4-tetrahydroquinazolinyl, octahydro-[2]pyridinyl, decahydro-cycloocta[c]furanyl, 1,2,3,4-tetrahydroisoquinolyl, 2-oxo-imidazolidinyl, and imidazolidinyl. In some embodiments, two moieties attached to a heteroatom may be taken together to form a heterocycloalkyl ring, such as when $R^5$ and $R^6$, taken together with the nitrogen atom to which they are attached, form a heterocycloalkyl ring. In certain of these embodiments, or 2 of the heterocycloalkyl ring carbon atoms may be replaced by other moieties which contain either one (—O—, —S—, —N(R)—) or two (—N(R)—C(=O)—, or —C(=O)—N(R)—) ring replacement atoms. When a moiety containing one ring replacement atom replaces a ring carbon atom, the resultant ring, after replacement of a ring atom by the moiety, will contain the same number of ring atoms as the ring before ring atom replacement.

As used herein, the term "spiroalkyl" refers to an optionally substituted alkylene diradical, both ends of which are bonded to the same carbon atom of the parent group to form a spirocyclic group. The spirocyclic group, as herein defined, has 3 to 20 ring atoms, or with 3 to 10 ring atoms. Exemplary spiroalkyl groups taken together with its parent group include, but are not limited to, 1-(1-methyl-cyclopropyl)-propan-2-one, 2-(1-phenoxy-cyclopropyl)-ethylamine, and 1-methyl-spiro[4.7]dodecane.

As used herein, "halo" and "halogen" each refers to a fluoro, chloro, bromo, or iodo moiety.

As used herein, "pseudohalo," and "pseudohalogen" refers to azide, cyano, isocyano, hydroxyl, sulfhydryl, isocyanate, thiocyanate, isothiocyanate, and the like.

Typically, substituted chemical moieties include one or more substituents that replace hydrogen. Exemplary substituents include, for example, halo (e.g., F, Cl, Br, I), alkyl, cycloalkyl, alkylcycloalkyl, cycloalkylalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N— substituted amino (—NHR"), —N,N-disubstituted amino (—N(R")R"), oxo (=O), carboxy (—COOH), —O—C(=O)R", alkoxycarbonyl (—C(=O)R"), —OR", —C(=O)OR", -(alkylene)-C(=O)—OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (—SR"), sulfonic acid (—SO$_3$H), phosphonic acid (—PO$_3$H), —P(=O)(OR")OR", —S(=O)R", —S(=O)$_2$R", —S(=O)$_2$NH$_2$, —S(=O)$_2$ NHR", —S(=O)$_2$NR"R", —NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like.

In relation to the aforementioned substituents, each moiety R" can be, independently, any of H, alkyl, cycloalkyl, alkenyl, aryl, aralkyl, heteroaryl, or heterocycloalkyl, or when two R" groups are attached to the same nitrogen atom within a Substituent, as herein above defined, R" and R" can be taken together with the nitrogen atom to which they are attached to form a 3- to 8-membered heterocycloalkyl ring, wherein one or two of the heterocycloalkyl ring carbon atoms independently may be optionally replaced by —O—, —S—, —SO, —SO$_2$—, —NH—, —N(alkyl)-, —N(acyl)-, —N(aryl)-, or —N(aroyl)-groups, for example.

As used herein, "cannabinoid" refers to any one of a group of naturally occurring compounds of related structure that may be isolable from *Cannabis sativa*, more commonly known as marijuana, and structurally modified derivatives thereof. Cannabinoids include for example, compounds such as $\Delta^9$-tetrahydrocannabinol, $\Delta^8$-tetrahydrocannabinol, cannabichromene, cannabicyclol, cannabidiol, cannabielsoin, cannabigerol, cannabinol, cannabitriol, nabilone, and nantradol, and numerous structural variants. Typically, cannabinoids are lipophilic in terms of their solubility.

As used herein, "side effect" refers to a consequence other than the one(s) for which an agent or measure is used, as the adverse effects produced by a drug, especially on a tissue or organ system other then the one sought to be benefited by its administration. In the case, for example, of cannabinoids, the term "side effect" may refer to such conditions as, for example, psychotropic effects, such as confusion, anxiety, panic, distortion of perception, fantasizing, sedation, inner unrest, irritability and insomnia, sweating, rhinorrhoea, loose stools, hiccups, dry mouth, tachycardia, ataxia, dizziness, orthostatic hypotension, and anorexia.

As used herein, "effective amount" refers to an amount of a compound as described herein that may be therapeutically effective to inhibit, prevent or treat the symptoms of particular disease, disorder or side effect. Such diseases, disorders and side effects include, but are not limited to, those pathological conditions associated with the binding of cannabinoid receptors (for example, in connection with the treatment and/or prevention of pain), wherein the treatment or prevention comprises, for example, agonizing the activity thereof by contacting cells, tissues or receptors with compounds of the disclosure. Thus, for example, the term "effective amount," when used in connection with cannabinoids, for example, for the treatment of pain, refers to the treatment and/or prevention of the painful condition. The term "effective amount", when used in connection with the disclosed cannabinoid receptor agonist compounds, refers to the treatment, reduction and/or prevention of side effects typically associated with cannabinoids including, for example, such side effects as those hereinabove mentioned.

As used herein, "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "in combination with", "combination therapy" and "combination products" refer, in certain embodiments, to the concurrent administration to a patient of cannabinoids and the compounds of the disclosure. When administered in combination, each component may be administered at the same time or sequentially in any order at different points in time. Thus, each component may be administered separately but sufficiently closely in time so as to provide the desired therapeutic effect.

As used herein, "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the disclosure may be dictated by (a) the unique characteristics of the active compound(s) and the particular therapeutic effect(s) to be achieved, and (b) the limitations inherent in the art of compounding such active compound(s).

As used herein, "hydrate" refers to a compound of the disclosure which is associated with water in the molecular form, i.e., in which the H—OH bond is not split, and may be represented, for example, by the formula $R.H_2O$, where R is a compound of the disclosure. A given compound may form more than one hydrate including, for example, monohydrates ($R.H_2O$) or polyhydrates ($R_n.H_2O$ wherein n is an integer >1) including, for example, dihydrates ($R_2.H_2O$), trihydrates ($R_3.H_2O$), and the like, or hemihydrates, such as, for example, $R_{n/2}.H_2O$, $R_{n/3}.H_2O$, $R_{n/4}.H_2O$ and the like wherein n is an integer.

As used herein, "solvate" refers to a compound of the disclosure which is associated with solvent in the molecular form, i.e., in which the solvent is coordinatively bound, and may be represented, for example, by the formula R.(solvent), where R is a compound of the disclosure. A given compound may form more than one solvate including, for example, monosolvates (R.(solvent)) or polysolvates (R.n (solvent)) wherein n is an integer >1) including, for example, disolvates (R.2(solvent)), trisolvates (R.3(solvent)), and the like, or hemisolvates, such as, for example, $R.n/_2$(solvent), $R.n/_3$(solvent), $R.n/_4$(solvent) and the like wherein n is an integer. Solvents herein include mixed solvents, for example, methanol/water, and as such, the solvates may incorporate one or more solvents within the solvate.

As used herein, "acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout may exist in alternate forms and such alternate forms are intended to be included within the scope of the compounds described and claimed in the application. Accordingly, reference herein to compounds of Formula I is intended to include reference to these alternate forms. For example, many amino-containing compounds can be used or prepared as an acid addition salt. Often such salts improve isolation and handling properties of the compound. For example, depending on the reagents, reaction conditions, and the like, compounds as described herein can be used or prepared, for example, as their hydrochloride or tosylate salts. Alternate forms of the compounds described herein also include, for example, isomorphic crystalline forms, all chiral and racemic forms, including stereoisomeric and partial stereoisomeric forms, N-oxides, hydrates, solvates, and acid salt hydrates.

Certain acidic or basic compounds of the disclosure may exist as zwitterions. All forms of the compounds, including free acid, free base and zwitterions, are contemplated to be within the scope of the disclosure. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

As used herein, "patient" refers to animals, including mammals, including humans.

As used herein, "agonist" refers to a ligand that produces a conformational change in the receptor and alters the equilibrium of the receptor's active and inactive states, which in turn induces a series of events, resulting in a measurable biological response. Agonists include, for example, conventional agonists, which exhibit positive receptor activity, and inverse agonists, which exhibit a negative intrinsic activity.

As used herein, "prodrug" refers to compounds specifically designed to maximize the amount of active species that reaches the desired site of reaction, which are of themselves typically inactive or minimally active for the activity desired, but through biotransformation are converted into biologically active metabolites.

As used herein, "stereoisomers" refers to compounds that have identical chemical constitution, but differ as regards the arrangement of the atoms or groups in space.

As used herein, "partial stereoisomer" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

As used herein, "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the disclosure does not depend upon the theoretical correctness of these formulae, in whole or in part. Thus, it is understood that the formulas used herein, as well as the chemical names attributed to the correspondingly indicated compounds, are not intended to limit the disclosure in any way, including restricting it to any specific tautomeric form or to any specific optical or geometric isomer, except where such stereochemistry is clearly defined.

Accordingly, the disclosure is directed, in part, to a new class of cannabinoid receptor modulator compounds, which are highly useful in connection with the binding of cannabinoid receptors. Compounds binding cannabinoid receptors may act as agonists, inverse agonists, and/or antagonists toward the cannabinoid receptors. In situations where a cannabimimetic compound or ligand agonizes one or more cannabinoid receptors, the resultant binding is believed to trigger an event or series of events in the cell that results in a change in the cell's activity, its gene regulation, or the signals that it sends to neighboring cells, similar to that of a cannabinoid. Thus, in some embodiments, the compounds of the disclosure may serve as preventatives or treatments of diseases or disorders in which cannabinoid receptors are implicated. In situations where a cannabimimetic compound or ligand antagonizes one or more cannabinoid receptors, the resultant binding typically occurs comparatively to a greater extent relative to that of the endogenous cannabinoid, but does not trigger one or more of the events of signal transduction. Compounds acting as inverse agonists are believed to bind more strongly to the inactive form of the receptor, thereby inhibiting the normal regulatory functions of the receptor and its endogenous regulatory ligands. Compounds with either inverse agonist or antagonist properties are highly useful, for example, in connection with the study of functions of cannabinoid receptors, which may result, for example, in the development of new cannabimimetic agonist compounds, such as those, for example, reported in Rinaldi-Carmona, M. et al., *Journal of Pharmacology and Experimental Therapeutics*, 1998, 284 (2), 644-650, the disclosure of which is hereby incorporated herein by reference, in its entirety.

The disclosed compounds and compositions relate to cannabinoids having electron-withdrawing (or electronegative) groups on, in or near the aromatic ring. These compounds and compositions have increased biological and pharmaceutical activities, both alone and in combination with other pharmaceutical agents. The compounds and compositions can be prepared by introducing electron withdrawing groups into natural or synthetic cannabinoids using synthetic procedures, using, for example, Friedel-Crafts acylation and/or alkylation conditions or by any other suitable means. The compounds and compositions can also be prepared through a total synthesis route starting from the appropriate materials.

CBD is known to delay the oxidation of THC to 11-Hydroxy THC by one or more members of the Cytochrome P450 (Cy-P450) family of enzymes. It is thought that CBD shows greater affinity for the enzyme than THC and therefore, the enzyme must first metabolize any CBD present before it can begin producing 11-Hydroxy THC. It was reasoned that a chemically modified CBD, more stable and less-easily oxidized by Cy-P450, could tie up this metabolic pathway indefinitely, thus prolonging and enhancing THC's beneficial effects while suppressing the negative effects of 11-Hydroxy THC, e.g. stoned, lethargic, mentally dull, paranoia, low blood sugar, and dry eyes and mouth. In addition, further oxidation of 11-Hydroxy THC leads to 11-Carboxy THC, which while inactive, causes lingering mental and physical dullness lasting for a few days, and longer in chronic users.

Thus, in one embodiment, the disclosure relates to compounds of Formula I:

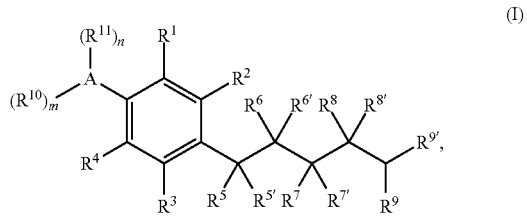

(I)

or a pharmaceutically acceptable salt thereof, wherein:

$R^1$, $R^2$, $R^3$ and $R^4$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —$OR^{12}$, —$C(=O)R^{12}$, —$C(=O)OR^{12}$, —$OC(=O)R^{12}$, —$OC(=O)OR^{12}$, —$NHC(=O)R^{12}$, —$N(R^{13})(R^{14})$, —$C(=O)N(R^{13})(R^{14})$, —$OC(=O)N(R^{13})(R^{14})$, —$NHC(=O)N(R^{13})(R^{14})$, and —$C(=O)CHR^{15}N(R^{13})(R^{14})$, each of which group may optionally be unsubstituted or substituted with one or more substituents, or $R^1$ and $R^2$, and/or $R^2$ and $R^5$, and/or $R^2$ and $R^6$, and/or $R^2$ and $R^7$, taken together with the carbon atoms to which each are attached, independently form a 4- to 8-membered ring, wherein 1 or 2 of the ring atoms independently are optionally replaced by —O—, —C(=O)—, —C(=O)O—, —NHC—, —N($C_1$-$C_6$)alkyl)-, —C(=O)NH—, or —C(=O)N($C_1$-$C_6$)alkyl)-, and $R^3$ and $R^4$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —$OR^{12}$, —$C(=O)R^{12}$, —$C(=O)OR^{12}$, —$OC(=O)R^{12}$, —$OC(=O)OR^{12}$, —$NHC(=O)R^{12}$, —$N(R^{13})(R^{14})$, —$C(=O)N(R^{13})(R^{14})$, —$OC(=O)N(R^{13})(R^{14})$, —$NHC(=O)N(R^{13})(R^{14})$, and —$C(=O)CHR^{15}N(R^{13})(R^{14})$, each of which group may optionally be unsubstituted or substituted with one or more substituents;

$R^5$, $R^{5'}$, $R^6$, $R^{6'}$, $R^7$, $R^{7'}$, $R^8$, $R^{8'}$, $R^9$, and $R^{9'}$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —$C(=O)R^{12}$, —$C(=O)OR^{12}$, —$OC(=O)R^{12}$, —$OC(=O)OR^{12}$, —$NHC(=O)R^{12}$, —$N(R^{13})(R^{14})$, —$C(=O)N(R^{13})(R^{14})$, —$OC(=O)N(R^{13})(R^{14})$, —NHC (=O)N($R^{13}$)($R^{14}$), and —C(=O)CHR$^{15}$N($R^{13}$)($R^{14}$), each of which group may optionally be unsubstituted or substituted with one or more substituents, or $R^5$, $R^{5'}$, and/or $R^6$, $R^{6'}$, and/or $R^7$, $R^{7'}$, and/or $R^8$, $R^{8'}$, and/or $R^9$, and $R^{9'}$ each independently form C=O, C=S, or C=NH, or $R^5$ and $R^6$, or $R^5$ and $R^7$, or $R^6$ and $R^7$, or $R^6$ and $R^8$, or $R^7$ and $R^8$, or $R^7$ and $R^9$, or $R^8$ and $R^9$ taken together with the carbon atoms to which each are attached, independently form a 4- to 8-membered ring, wherein 1 or 2 of the ring atoms independently are optionally replaced by —O—, —C(=O)—, —C(=O)O—, —NH—, —N($C_1$-$C_6$)alkyl)-, —(C(=O)NH—, or —(C(=O)N($C_1$-$C_6$)alkyl)-, and the remainder of $R^5$ and $R^6$, or $R^5$ and $R^7$, or $R^6$ and $R^7$, or $R^6$ and $R^8$, or $R^7$ and $R^8$, or $R^7$ and $R^9$, or $R^8$ and $R^9$, are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)OR$^{12}$, —NHC(=O)R$^{12}$, —N($R^{13}$)($R^{14}$), —C(=O)N($R^{13}$)($R^{14}$), —OC(=O)N($R^{13}$)($R^{14}$), —NHC(=O)N($R^{13}$)($R^{14}$), and —C(=O)CHR$^{15}$N($R^{13}$)($R^{14}$), each of which group may optionally be unsubstituted or substituted with one or more substituents;

A is independently selected from alkyl, alkenyl, alkynyl, cycloalkyl, cycloalkenyl, heterocycloalkyl, alkoxy, aryl, aralkyl, heteroaryl, heteroaralkyl, 5- or 6-membered heterocyclic ring, 5- or 6-membered heteroaryl ring, and a 6-membered aryl ring, each of which group may be optionally unsubstituted or substituted with one or more substituents;

$R^{10}$ and $R^{11}$ are each independently selected from hydrogen, hydroxyl, halogen, alkyl, alkenyl, alkynyl, cycloalkyl, spiroalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)OR$^{12}$, —NHC(=O)R$^{12}$, —N($R^{13}$)($R^{14}$), —C(=O)N($R^{13}$)($R^{14}$), —OC(=O)N($R^{13}$)($R^{14}$), —NHC(=O)N($R^{13}$)($R^{14}$), and —C(=O)CHR$^{15}$N($R^{13}$)($R^{14}$), each of which group may optionally be unsubstituted or substituted with one or more substituents, or $R^{10}$ and $R^{11}$, taken together with the atom to which they are attached, independently form a substituted or unsubstituted 4 to 8 membered cyclic or heterocyclic ring, or a 5 membered heteroaryl ring, or a 6 membered aryl ring;

m and n are each independently an integer ranging from 0 to 5;

$R^{12}$ is each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —N($R^{13}$)($R^{14}$), —C(=O)N($R^{13}$)($R^{14}$), —OC(=O)N($R^{13}$)($R^{14}$), —NHC(=O)N($R^{13}$)($R^{14}$), and —C(=O)CHR$^{15}$N($R^{13}$)($R^{14}$), each of which group may optionally be unsubstituted or substituted with one or more substituents;

$R^{13}$ and $R^{14}$ are each independently selected from hydrogen, alkyl, alkenyl, alkynyl, cycloalkyl, cycloalkenyl, heterocycloalkyl, aryl, aralkyl, heteroaryl, and heteroaralkyl, or $R^{13}$ and $R^{14}$, taken together with the nitrogen atom to which they are attached, independently form a 4- to 8-membered heterocyclic ring wherein 1 or 2 of the ring atoms independently are optionally replaced by —O—, —S—, —S(=O)—, —S(=O)$_2$—, —NH—, —N(alkyl)-, —N(C(=O)R$^{12}$)—, or —N(S(=O)$_2$—R$^{12}$)—; and $R^{15}$ is independently selected from hydrogen, alkyl, alkenyl, alkynyl, cycloalkyl, cycloalkenyl, heterocycloalkyl, aryl, aralkyl, heteroaryl, and heteroaralkyl.

In another embodiment, the disclosure relates to compounds of Formula I, wherein A has formula:

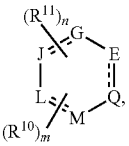

wherein Q, E, G, J, L, and M are each independently selected from —C—, —CH—, —CR10-, —CR11-, —C=, —N—, —NH—, —NR10- —NR11-, —N=, —O—, and —S—, or one of Q, E, G, J, L, and M is and absent, and the other of Q, E, G, J, L, and M are each independently selected from —C—, —CH—, —CR10-, —CR11-, —C=, —N—, —NH—, —NR10- —NR11-, —N=, —O—, and —S—.

In another embodiment, the disclosure relates to compounds of Formula I, wherein $R^1$ and $R^4$ are each independently selected from hydrogen, —OR$^{12}$, and —N($R^{13}$)($R^{14}$).

In another embodiment, the disclosure relates to compounds of Formula I, wherein $R^1$ and $R^4$ are each independently selected from hydrogen, —OH, —O($C_1$-$C_6$)alkyl, —NH($C_1$-$C_6$)alkyl, and —N[($C_1$-$C_6$)alkyl]$_2$.

In another embodiment, the disclosure relates to compounds of Formula I, wherein $R^2$ and $R^3$ are each independently selected from hydrogen, alkyl, —C(=O)R$^{12}$, —C(=O)OR$^{12}$, —CN, —C(=O)N($R^{13}$)($R^{14}$), and —C(=O)CHR$^{15}$N($R^{13}$)($R^{14}$).

In another embodiment, the disclosure relates to compounds of Formula I, wherein $R^2$ and $R^3$ are each independently selected from hydrogen, —($C_1$-$C_6$)alkyl, —C(=O)($C_1$-$C_6$)alkyl, —C(=O)O($C_1$-$C_6$)alkyl, —CN, —C(=O)NH($C_1$-$C_6$)alkyl, —C(=O)N[($C_1$-$C_6$)alkyl]$_2$, —C(=O)CHR$^{15}$NH($C_1$-$C_6$)alkyl, and —C(=O)CHR$^{15}$N[($C_1$-$C_6$)alkyl]$_2$.

In another embodiment, the disclosure relates to compounds of Formula I, wherein $R^1$ and $R^4$ are each independently selected from —OH and —O($C_1$-$C_6$)alkyl; and $R^2$ and $R^3$ are each independently selected from hydrogen and —C(=O)($C_1$-$C_6$)alkyl.

In another embodiment, the disclosure relates to compounds of Formula I, wherein $R^5$, $R^{5'}$, $R^6$, $R^{6'}$, $R^7$, $R^{7'}$, $R^8$, $R^{8'}$, $R^9$, and $R^{9'}$ are each independently selected from hydrogen, —($C_1$-$C_6$)alkyl, F, Cl, Br, I, —OH, and —O($C_1$-$C_6$)alkyl.

In another embodiment, the disclosure relates to compounds of Formula I, wherein $R^{10}$ and $R^{11}$ are each independently selected from hydrogen and ($C_1$-$C_6$)alkyl.

In another embodiment, the disclosure relates to compounds of Formula I, wherein $R^{10}$ and $R^{11}$ are each independently selected from hydrogen, —CH$_3$, —CH$_2$CH$_3$, —CH=CH$_2$, —CH$_2$CH$_2$CH$_3$, —CH=CCH$_3$, —CH$_2$CH=CH$_2$, —C=CHCH$_2$CH$_3$, —CH$_2$CH=CHCH$_3$, —CH$_2$CH$_2$CH=CH, —CH$_2$CH(CH$_3$)$_2$, —CH=C(CH$_3$)$_2$, —CH$_2$C(=CH$_2$)(CH$_3$), —CH(CH$_3$)CH$_2$CH$_3$, —C(=CH$_2$)CH$_2$CH$_3$, and —CH(CH$_3$)C=CH$_2$.

In another embodiment, the disclosure relates a pharmaceutical composition, comprising a pharmaceutically acceptable carrier and one or more compounds of Formula I.

In another embodiment, the disclosure relates a pharmaceutical composition, comprising a pharmaceutically acceptable carrier and one or more compounds of Formula I, further comprising at least one cannabinoid.

In another embodiment, the disclosure relates a pharmaceutical composition, comprising a pharmaceutically acceptable carrier and one or more compounds of Formula I, further comprising at least one cannabinoid wherein the cannabinoid is Δ$^9$-tetrahydrocannabinol or cannabidiol.

In another embodiment, the disclosure relates a pharmaceutical composition, comprising a pharmaceutically acceptable carrier and one or more compounds of Formula I, further comprising at least one opioid.

In another embodiment, the disclosure relates a pharmaceutical composition, comprising a pharmaceutically acceptable carrier and one or more compounds of Formula I, further comprising at least one opioid, wherein the at least one opioid is selected from alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil, tramadol, and mixtures thereof.

In another embodiment, the disclosure relates a pharmaceutical composition, comprising a pharmaceutically acceptable carrier and one or more compounds of Formula I, further comprising at least one analgesic.

In another embodiment, the disclosure relates a pharmaceutical composition, comprising a pharmaceutically acceptable carrier and one or more compounds of Formula I, further comprising at least one analgesic, wherein the analgesic is selected from a COX2 inhibitor, aspirin, acetaminophen, ibuprofen, naproxen, and mixtures thereof.

In another embodiment, the disclosure relates a pharmaceutical composition, comprising a pharmaceutically acceptable carrier and one or more compounds of Formula I, further comprising at least one agent selected from an anti-seizure agent, an anti-depressant, an NMDA receptor antagonist, an ion channel antagonist, a nicotinic receptor agonist, an anti-Parkinson's agent, and mixtures thereof.

In another embodiment, the disclosure relates a pharmaceutical composition, comprising a pharmaceutically acceptable carrier and one or more compounds of Formula I, further comprising at least one agent selected from an anti-seizure agent, an anti-depressant, an NMDA receptor antagonist, an ion channel antagonist, a nicotinic receptor agonist, an anti-Parkinson's agent, and mixtures thereof, wherein the anti-seizure agent is selected from carbamazepine, gabapentin, lamotrigine, phenytoin, and mixtures thereof; the anti-depressant is amitriptyline; and the anti-Parkinson's agent is selected from deprenyl, amantadine, levodopa, or carbidopa, and mixtures thereof.

In another embodiment, the disclosure relates a method of preparing a compound of Formula I:

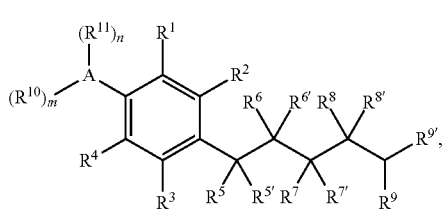

(I)

or a pharmaceutically acceptable salt thereof, comprising:
a) reacting a compound of Formula II with an acylation reagent to provide the compound of Formula I:

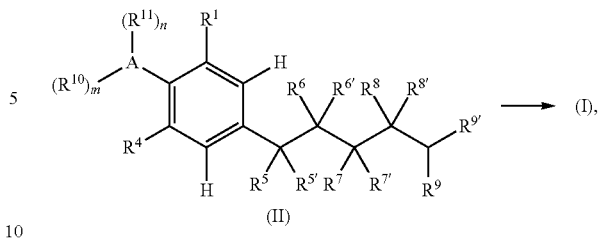

(II)

wherein:
$R^1$, $R^2$, $R^3$ and $R^4$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)OR$^{12}$, —NHC(=O)R$^{12}$, —N(R$^{13}$)(R$^{14}$), —C(=O)N(R$^{13}$)(R$^{14}$), —OC(=O)N(R$^{13}$)(R$^{14}$), —NHC(=O)N(R$^{13}$)(R$^{14}$), and —C(=O)CHR$^{15}$N(R$^{13}$)(R$^{14}$), each of which group may optionally be unsubstituted or substituted with one or more substituents, or $R^1$ and $R^2$, and/or $R^2$ and $R^5$, and/or $R^2$ and $R^6$, and/or $R^2$ and $R^7$, taken together with the carbon atoms to which each are attached, independently form a 4- to 8-membered ring, wherein 1 or 2 of the ring atoms independently are optionally replaced by —O—, —(C(=)—, —(C(=O)O—, —NH—, —N(C$_1$-C$_6$)alkyl)-, —(C(=O)NH—, or —(C(=O)N(C$_1$-C$_6$)alkyl)-, and $R^3$ and $R^4$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)OR$^{12}$, —NHC(=O)R$^{12}$, —N(R$^{13}$)(R$^{14}$), —C(=O)N(R$^{13}$)(R$^{14}$), —OC(=O)N(R$^{13}$)(R$^{14}$), —NHC(=O)N(R$^{13}$)(R$^{14}$), and —C(=O)CHR$^{15}$N(R$^{13}$)(R$^{14}$), each of which group may optionally be unsubstituted or substituted with one or more substituents;

$R^5$, $R^{5'}$, $R^6$, $R^{6'}$, $R^7$, $R^{7'}$, $R^8$, $R^{8'}$, $R^9$, and $R^{9'}$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)OR$^{12}$, —NHC(=O)R$^{12}$, —N(R$^{13}$)(R$^{14}$), —C(=O)N(R$^{13}$)(R$^{14}$), —OC(=O)N(R$^{13}$)(R$^{14}$), —NHC(=O)N(R$^{13}$)(R$^{14}$), and —C(=O)CHR$^{15}$N(R$^{13}$)(R$^{14}$), each of which group may optionally be unsubstituted or substituted with one or more substituents, or $R^5$, $R^{5'}$, and/or $R^6$, $R^{6'}$, and/or $R^7$, $R^{7'}$, and/or $R^8$, $R^{8'}$, and/or $R^9$, and $R^{9'}$ each independently form C=O, C=S, or C=NH, or $R^5$ and $R^6$, or $R^5$ and $R^7$, or $R^6$ and $R^7$, or $R^6$ and $R^8$, or $R^7$ and $R^8$, or $R^7$ and $R^9$, or $R^8$ and $R^9$ taken together with the carbon atoms to which each are attached, independently form a 4- to 8-membered ring, wherein 1 or 2 of the ring atoms independently are optionally replaced by —O—, —(C(=O)—, —(C(=O)O—, —NH—, —N(C$_1$-C$_6$)alkyl)-, —(C(=O)NH—, or —(C(=O)N(C$_1$-C$_6$)alkyl)-, and the remainder of $R^5$ and $R^6$, or $R^5$ and $R^7$, or $R^6$ and $R^7$, or $R^6$ and $R^8$, or $R^7$ and $R^8$, or $R^7$ and $R^9$, or $R^8$ and $R^9$, are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —OR$^{12}$, —C(=O)R$^{12}$, —C(=O)OR$^{12}$, —OC(=O)R$^{12}$, —OC(=O)OR$^{12}$, —NHC(=O)R$^{12}$, —N(R$^{13}$)(R$^{14}$), —C(=O)N(R$^{13}$)(R$^{14}$), —OC(=O)N(R$^{13}$)(R$^{14}$), —NHC(=O)N(R$^{13}$)(R$^{14}$), and —C(=O)CHR$^{15}$N(R$^{13}$)

($R^{14}$), each of which group may optionally be unsubstituted or substituted with one or more substituents;

A is independently selected from alkyl, alkenyl, alkynyl, cycloalkyl, cycloalkenyl, heterocycloalkyl, alkoxy, aryl, aralkyl, heteroaryl, heteroaralkyl, 5- or 6-membered heterocyclic ring, 5- or 6-membered heteroaryl ring, and a 6-membered aryl ring, each of which group may be optionally unsubstituted or substituted with one or more substituents;

$R^{10}$ and $R^{11}$ are each independently selected from hydrogen, hydroxyl, halogen, alkyl, alkenyl, alkynyl, cycloalkyl, spiroalkyl, cycloalkenyl, heterocycloalkyl, alkoxy, aryl, aralkyl, heteroaryl, heteroaralkyl, nitro, cyano, —$OR^{12}$, —$C(=O)R^{12}$, —$C(=O)OR^{12}$, —$OC(=O)R^{12}$, —$OC(=O)OR^{12}$, —$NHC(=O)R^{12}$, —$N(R^{13})(R^{14})$, —$C(=O)N(R^{13})(R^{14})$, —$OC(=O)N(R^{13})(R^{14})$, —$NHC(=O)N(R^{13})(R^{14})$, and —$C(=O)CHR^{15}N(R^{13})(R^{14})$, each of which group may optionally be unsubstituted or substituted with one or more substituents, or $R^{10}$ and $R^{11}$, taken together with the atom to which they are attached, independently form a substituted or unsubstituted 4 to 8 membered cyclic or heterocyclic ring, or a 5 membered heteroaryl ring, or a 6 membered aryl ring;

m and n are each independently an integer ranging from 0 to 5;

$R^{12}$ is each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, —$N(R^{13})(R^{14})$, —$C(=O)N(R^{13})(R^{14})$, —$OC(=O)N(R^{13})(R^{14})$, —$NHC(=O)N(R^{13})(R^{14})$, and —$C(=O)CHR^{15}N(R^{13})(R^{14})$, each of which group may optionally be unsubstituted or substituted with one or more substituents;

$R^{13}$ and $R^{14}$ are each independently selected from hydrogen, alkyl, alkenyl, alkynyl, cycloalkyl, cycloalkenyl, heterocycloalkyl, aryl, aralkyl, heteroaryl, and heteroaralkyl, or $R^{13}$ and $R^{14}$, taken together with the nitrogen atom to which they are attached, independently form a 4- to 8-membered heterocyclic ring wherein 1 or 2 of the ring atoms independently are optionally replaced by —O—, —S—, —S(=O)—, —S(=O)$_2$—, —NH—, —N(alkyl)-, —N(C(=O)$R^{12}$)—, or —N(S(=O)$_2$—$R^{12}$)—; and $R^{15}$ is independently selected from hydrogen, alkyl, alkenyl, alkynyl, cycloalkyl, cycloalkenyl, heterocycloalkyl, aryl, aralkyl, heteroaryl, and heteroaralkyl.

In another embodiment, the disclosure relates a method of preparing a compound of Formula I, or a pharmaceutically acceptable salt thereof, comprising: a) reacting a compound of Formula II with an acylation reagent to provide the compound of Formula I, wherein the acylation reagent is an anhydride or an acid halide or pseudohalide.

In some embodiments, and acylation catalyst can be used including but not limited to aluminum chloride (AlCl$_3$), methanesulfonic acid (MSA), trifluoromethanesulfonic acid (TfOH) and the like. In other embodiments, acylation can occur without a catalyst being present. In some embodiments, lowered or elevated temperatures can be used for the acylation, for example, temperatures ranging from about −80° C. to about 260° C.

The compounds employed in the methods of the disclosure may exist in prodrug form. As used herein, "prodrug" is intended to include any covalently bonded carriers which release the active parent drug, for example, as according to Formula I or other formulas or compounds employed in the methods of the disclosure in vivo when such prodrug is administered to a mammalian subject. Since prodrugs are known to enhance numerous desirable qualities of pharmaceuticals (e.g., solubility, bioavailability, manufacturing, etc.) the compounds employed in the disclosed methods may, if desired, be delivered in prodrug form. Thus, the disclosure contemplates methods of delivering prodrugs. Prodrugs of the compounds employed in the disclosure, for example Formula I, may be prepared by modifying functional groups in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds can be combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosure of which is hereby incorporated herein by reference, in its entirety.

Although the compounds of the disclosure may be administered as the pure chemicals, they can present the active ingredient as a pharmaceutical composition. Thus, the disclosure further provides a pharmaceutical composition comprising one or more of the cannabinoid receptor modulator compounds of the disclosure, together with one or more pharmaceutically acceptable carriers therefore and, optionally, other therapeutic and/or prophylactic ingredients. The carrier(s) include being acceptable in the sense of being compatible with the other ingredients of the composition and not deleterious to the recipient thereof.

In accordance with certain embodiments of the disclosure, the disclosed compositions may further comprise at least one cannabinoid. A variety of cannabinoids are available that may be suitable for use in the disclosed methods and compositions. Generally speaking, it is only necessary that the cannabinoid provide the desired effect (for example, pain alleviation), and be capable of being incorporated into the disclosed combination products and methods (discussed in detail below). In embodiments, the disclosed methods and compositions may involve a cannabinoid or a cannabinmimetic selected from $\Delta^9$-tetrahydrocannabinol and cannabidiol, and mixtures thereof.

Alternatively, in accordance with certain embodiments of the disclosure, the disclosed compositions may further comprise at least one opioid. A wide variety of opioids are available that may be suitable for use in the disclosed methods and compositions. Generally speaking, it is only necessary that the opioid provide the desired effect (for example, pain alleviation), and be capable of being incorporated into the disclosed combination products and methods (discussed in detail below). In embodiments, the disclosed methods and compositions may involve an opioid selected from alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil and/or tramadol. Moreover, the opioid is selected from morphine, codeine, oxycodone, hydrocodone, dihydrocodeine, propoxyphene, fentanyl, tramadol, and mixtures thereof.

Alternatively, in accordance with certain other embodiments of the disclosure, the disclosed compositions may further comprise at least one analgesic, such as for example, COX2 inhibitors, aspirin, acetaminophen, ibuprofen, naproxen, and the like, and mixtures thereof. Generally speaking, it is only necessary that the analgesic provide the desired effect (for example, pain alleviation), and be capable of being incorporated into the disclosed combination products and methods (discussed in detail below).

Alternatively, in accordance with still other embodiments of the disclosure, the disclosed compositions may further comprise at least one therapeutic agent selected from the group consisting of anti-seizure agents, such as for example, carbamazepine, gabapentin, lamotrigine, and phenytoin, anti-depressants such as, for example, amitriptyline, NMDA receptor antagonists, ion channel antagonists, nicotinic receptor agonists, and anti-Parkinson's agents, such as for example, Deprenyl, Amantadine, Levodopa, and Carbidopa. Generally speaking, it is only necessary that the anti-seizure agent, anti-depressant, NMDA receptor antagonist, ion channel antagonist, nicotinic receptor agonist, or anti-Parkinson's agent provide the desired effect (for example, inhibition of seizures, alleviation of depression, and the like), and be capable of being incorporated into the disclosed combination products and methods (discussed in detail below).

The compounds of the disclosure may be administered in an effective amount by any of the conventional techniques well-established in the medical field. The compounds employed in the methods of the disclosure including, for example, the compounds of Formula I may be administered by any means that results in the contact of the active agents with the agents' site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Compounds of the disclosure can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic, inhalation, volatilization, vaping, and smoking.

The active compound may be orally administered, for example, with an inert diluent or with an assimilable edible carrier, or it may be enclosed in hard shell or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is such that a suitable dosage will be obtained. The compositions or preparations according to the disclosure may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl- and propyl-parabens as preservatives, a dye and flavoring, such as cherry or orange flavor. Of course, any material used in preparing any dosage unit form is pharmaceutically pure and substantially non-toxic in the amounts employed. In addition, the active compound may be incorporated into sustained-release preparations and formulations.

The active compound may also be administered parenterally or intraperitoneally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form can be sterile and fluid to provide easy syringability. It is stable under the conditions of manufacture and storage and can be preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, include isotonic agents can be included, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the methods of preparation may include vacuum drying and the freeze-drying technique that yields a powder of the active ingredient, plus any additional desired ingredient from the previously sterile-filtered solution thereof.

The therapeutic compounds of the disclosure may be administered to a patient alone or in combination with a pharmaceutically acceptable carrier. As noted above, the relative proportions of active ingredient and carrier may be determined, for example, by the solubility and chemical nature of the compounds, chosen route of administration and standard pharmaceutical practice.

The dosage of the compounds of the disclosure that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The combination products of the disclosure, such as pharmaceutical compositions comprising cannabinoids and/or opioids in combination with the compounds of Formula I may be in any dosage form, such as those described herein, and can also be administered in various ways, as described herein. In an embodiment, the combination products of the disclosure are formulated together, in a single dosage form (that is, combined together in one capsule, tablet, powder, or liquid, etc.). When the combination products are not formulated together in a single dosage form, the cannabinoid and/or opioid compounds and the compounds of Formula I may be administered at the same time (that is, together), or in any order. When not administered at the same time, the administration of a cannabinoid and/or opioid and the compounds of Formula I occurs less than about one hour apart, or less than about 30 minutes apart, or less than about 15 minutes apart, or less than about 5 minutes apart. The administration of the combination products of the disclosure can be oral, although other routes of administration, as described above, are contemplated to be within the scope of the disclosure. Although the cannabinoids and/or opioids and the compounds of Formula I can both administered in the same fashion (that is, for example, both orally), if desired, they may each be administered in different fashions (that is, for example, one component of the combination product may be administered orally, and another component may be administered intravenously). The dosage of the combination products of the disclosure may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of the disclosure will be readily ascertainable by one skilled in the art, once armed with the disclosure, by way of general guidance, where a cannabinoid and/or opioid compound is combined with the compounds of Formula I, for example, typically a daily dosage may range from about 0.01 to about 100 milligrams of the cannabinoid and/or opioid (and all combinations and subcombinations of ranges therein) and about 0.001 to about 100 milligrams of the compounds of Formula I (and all combinations and subcombinations of ranges therein), per kilogram of patient body weight. The daily dosage may be about 0.1 to about 10 milligrams of the cannabinoid and/or opioid and about 0.01 to about 10 milligrams of the compounds of Formula I per kilogram of patient body weight, or the daily dosage may be about 1.0 milligrams of the cannabinoid and/or opioid and about 0.1 milligrams of the compounds of Formula I per kilogram of patient body weight. With regard to a typical dosage form of this type of combination product, such as a tablet, the cannabinoid compounds (e.g. $\Delta^9$-tetrahydrocannabinol or cannabidiol) and/or the opioid compounds (e.g., morphine) and generally may be present in an amount of about 15 to about 200 milligrams, and the compounds of Formula I in an amount of about 0.1 to about 4 milligrams.

Particularly when provided as a single dosage form, the potential exists for a chemical interaction between the combined active ingredients, for example, a cannabinoid and the compounds of Formula I. For this reason, the dosage forms of the combination products of the disclosure are formulated such that although the active ingredients are combined in a single dosage form, the physical contact between the active ingredients is minimized (that is, reduced).

In order to minimize contact, one embodiment of the disclosure where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of the disclosure where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropylmethylcellulose (HPMC) or other appropriate materials as known in the art, in order to further separate the active components. The polymer coating serves to form an additional barrier to interaction with the other component.

Dosage forms of the combination products of the disclosure wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the disclosure can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the disclosure, whether administered in a single dosage form or administered in separate forms but at the same time by the same manner, will be readily apparent to those skilled in the art, once armed with the disclosure.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The dose may also be provided by controlled release of the compound, by techniques well known to those in the art.

Pharmaceutical kits useful in, for example, the treatment of pain, which comprise a therapeutically effective amount of a cannabinoid and/or opioid along with a therapeutically effective amount of one or more compounds of the disclosure, in one or more sterile containers, are also within the ambit of the disclosure. Sterilization of the container may be carried out using conventional sterilization methodology well known to those skilled in the art. The sterile containers of materials may comprise separate containers, or one or more multi-part containers, as exemplified by the UNIV-IAL™ two-part container (available from Abbott Labs, Chicago, Ill.), as desired. The opioid or cannabinoid compound and the compound of Formula I, may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The compounds of the disclosure may be used in methods to bind cannabinoid receptors including CB1 or CB2 cannabinoid receptors. Such binding may be accomplished by contacting the receptor with an effective amount of one or more compounds of Formula I. The cannabinoid receptors may be located in the central nervous system or located peripherally to the central nervous system or in both locations. The contacting step conducted in an aqueous medium, at a physiologically relevant ionic strength, pH, and the like.

In certain embodiments, the compounds, pharmaceutical compositions and methods of the disclosure may involve a peripheral cannabinoid receptor agonist compound. The term "peripheral" designates that the compound acts primarily on physiological systems and components external to the central nervous system. In one form, the peripheral receptor agonist compounds employed in the methods of the disclosure exhibit high levels of activity with respect to peripheral nerve tissue, while exhibiting reduced, and having substantially no CNS activity. The phrase "substantially no CNS activity," as used herein, means that less than about 20% of the pharmacological activity of the compounds employed in the disclosed methods is exhibited in the CNS, including less than about 15%, or less than about 10%, or less than about 5%, or 0%, of the pharmacological activity of the compounds employed in the disclosed methods is exhibited in the CNS.

Furthermore, in certain embodiments of the disclosure where the compound is administered to agonize the peripheral cannabinoid receptors does not substantially cross the blood-brain barrier and thereby reduces the classical central side effects as observed for blood-brain penetrating cannabinoid agonists such as $\Delta^9$-tetrahydrocannabinol ($\Delta^9$-THC).

The central side effects of blood brain penetrating cannabinoid agonists limits their clinical utility, such as their use in the relief of pain. The phrase "does not substantially cross," as used herein, means that less than about 30% by weight of the compound employed in the disclosed methods crosses the blood-brain barrier, including less than about 15% by weight, or less than about 10% by weight, or less than about 5% by weight or 0% by weight of the compound crosses the blood-brain barrier. Selected compounds can be evaluated for CNS penetration by determining plasma and brain levels following i.v. administration.

In embodiments, the compounds of the disclosure may exhibit activity toward cannabinoid receptors, including binding thereto. The disclosed compounds are agonists toward cannabinoid receptors. Thus, in certain embodiments, the disclosure is directed, in part, to methods of binding cannabinoid receptors in a patient in need thereof, comprising the step of administering to said patient a composition comprising an effective amount of one or more compounds of the disclosure, including one or more compounds of Formula I. In one form, cannabinoid receptors which may be bound by the disclosed compounds are CB1 and/or CB2 cannabinoid receptors. In certain embodiments, the cannabinoid receptors so bound are located in the central nervous system. In other embodiments, cannabinoid receptors so bound are located peripherally to the central nervous system. Also, in some embodiments, the disclosed compounds may selectively bind the CB2 cannabinoid receptors relative to the CB1 receptors. Alternatively, the disclosed compounds may selectively bind the CB1 cannabinoid receptors relative to the CB2 receptors. Also, in some forms, the disclosed compounds do not substantially cross the blood-brain barrier.

Due to the activity of compounds of the disclosure towards cannabinoid receptors, the disclosure further contemplates their use in the treatment or prevention of diseases which are associated with cannabinoid receptors. The disclosed compounds may be useful in the treatment or prevention of a disease or disorder selected from the group consisting of pain, a gastrointestinal disorder, a genitourinary disorder, inflammatory disorders, glaucoma, an autoimmune disease, an ischemic condition, an immune-related disorder, and a neurodegenerative disease.

In embodiments involving the treatment or prevention of pain, the pain may be inflammatory pain, neuropathic pain, visceral pain, surgical pain, including pain which occurs during surgery or pain which occurs after surgery (i.e., postsurgical pain), or cancer related pain. In certain embodiments, the present pain ameliorating methods may further comprise the administration to the patient of at least on opioid in the form of combination products and/or combination therapy. Suitable opioids include, for example, alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil or tramadol, and mixtures thereof. In embodiments involving the treatment or prevention of neuropathic pain, the disclosed methods may further comprise administering to the patient codeine, carbamazepine, gabapentin, lamotrigine, phenytoin, amitriptyline, an NMDA receptor antagonist, an ion channel antagonist, or a nicotinic receptor agonist, or a mixture thereof, in the form of combination products and/or combination therapy.

Gastrointestinal disorders which may be treated with the disclosed compounds and methods include, for example, nausea, vomiting, loss of appetite, cachexia, diarrhea, inflammatory bowel disease, or irritable bowel syndrome.

Genitourinary disorders which may be treated with the disclosed compounds and methods include, for example, bladder dysfunction or nephritis.

Auto-immune diseases which may be treated with the disclosed compounds and methods include, for example, multiple sclerosis, rheumatoid arthritis, psoriasis, Crohn's disease, systemic lupus erythematosus, myasthenia gravis, diabetes mellitus type I, osteoporosis, or a combination thereof.

Ischemic conditions which may be treated with the disclosed compounds and methods include, for example, renal ischemia, cerebral stroke, cerebral ischemia, or a combination thereof.

Immune-related disorders which may be treated with the disclosed compounds and methods include, for example is asthma, chronic obstructive pulmonary disorder, emphysema, bronchitis, allergy, tissue rejection in organ transplants, celiac disease, Sjögren's syndrome, or a combination thereof.

Neurodegenerative diseases which may be treated with the disclosed compounds and methods include, for example, Parkinson's disease, Alzheimer's disease, Huntington's disease, amyotrophic lateral sclerosis, or a combination thereof. In certain embodiments, these methods may further comprise the administration to the patient of deprenyl, amantadine, levodopa, or carbidopa, in the form of combination products and/or combination therapy.

Ischemic or reperfusion effect which may be treated with the disclosed compounds and methods include, for example, arrhythmia or hypertension.

In other embodiments, the disclosure is directed, in part, to methods of inducing apoptosis in malignant cells, comprising the step of contacting said cells with an effective amount of a disclosed compound. In certain embodiments, apoptosis occurs in vitro. In other more embodiments, apoptosis occurs in vivo.

In still other embodiments, the disclosure is directed to methods for modulating appetite, comprising the step of administering to a patient in need thereof, an effective amount of a cannabinoid receptor agonist compound. In certain of these embodiments the modulation comprises stimulating appetite.

Methods of Preparation

As shown in Scheme I, CBD (I) was hydrogenated using known literature procedures to remove the double bonds present in the cyclohexene ring and the attached isopropenyl group. This reduction provided Tetrahydro CBD (II), with the 11-methyl group now being non-allylic. Tetrahydro CBD (II) showed slower oxidation by Cy-P450 and a resulting increase in CBD activity, approximately double in effect and duration, but lasting only a few minutes. Reaction of Tetrahydro CBD (II) with acetic anhydride at elevated temperatures followed by hydrolysis, introduced an acetyl group at the 2' position on the aromatic ring, i.e. Tetrahydro 2'-acetyl CBD (III). This compound had an enhanced CBD effect, preventing formation of 11-Hydroxy THC for about one hour. The next homolog, prepared from propionic anhydride, delayed THC metabolism for up to 48 hours. Other homologs tested showed activities ranging from 3 to 12 hours.

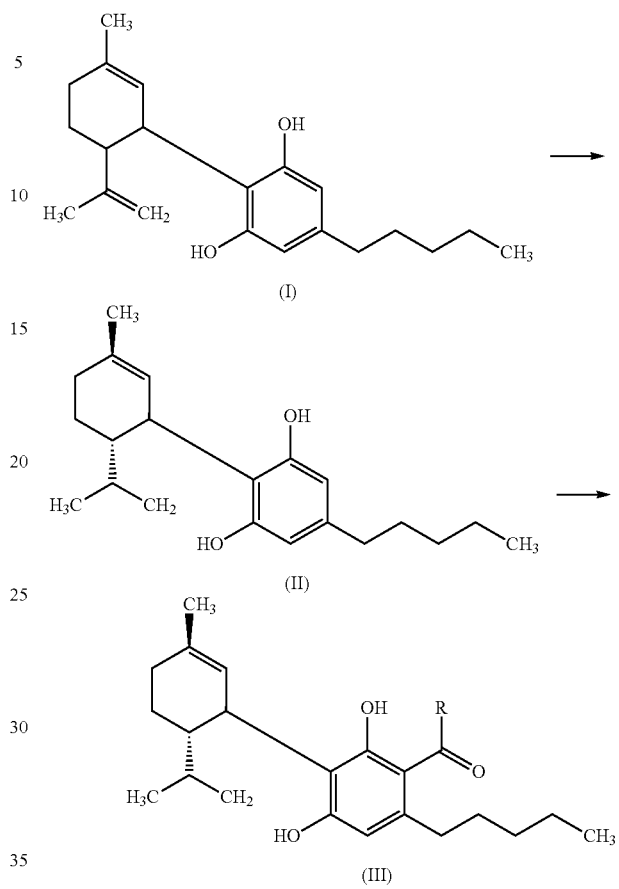

SCHEME I

The metabolism of these compounds appears to be at the R group of the introduced keto functionality. Cy-P450 oxidation of THC was slowed or prevented in the presence of these compounds. It is thought that the electron withdrawing nature of the keto group stabilizes the aromatic ring against oxidation of the resorcinol like system.

The disclosed compounds and compositions have been shown in individual trials to have strong anti-inflammatory properties at effective doses of about 5-15 mg in treating muscle and tendon pain and injury. Healing time appears to be reduced by about 50-70%. Results with back pain, muscle pulls, and strained tendons are generally favorable. A concussion patient presenting with significant nausea received complete relief within 4 hours of a 20 mg dose.

The combination of THC with the disclosed compounds and compositions is even more powerful. First, at recreational (high) doses of THC (about 20-50* mg THC), users experience slight mood enhancement without mental or physical impairment and are productive and energetic in their normal activities. Depending on which homolog, this effect may be prolonged from about 4-24 hours.

At lower THC levels (micro-doses of about 5-10 mg THC), post-surgical patients achieved pain relief up to that of morphine without opioid complications, e.g. no tolerance, addiction, mental or physical impairment, withdrawal, etc., and definite reduction in healing times (>>50%). Very little if any THC-like effects were experienced at these levels. An MS patient claimed complete freedom from symptoms for up to 2-days from each single usage (and ⅔rds less THC consumption).

Other features of the disclosure will become apparent in the course of the following descriptions of exemplary embodiments which are given for illustration of the disclosure and are not intended to be limiting thereof. The disclosure will now be illustrated by reference to the following specific, non-limiting examples. Those skilled in the art of organic synthesis may be aware of still other synthetic routes to the disclosed compounds. The reagents and intermediates used herein are either commercially available or prepared according to standard literature procedures, unless otherwise described.

Experimental Procedures

Materials: All chemicals were reagent grade and unless otherwise specified purchased from Sigma-Aldrich or other well known commercial vendors and used without further purification. All reactions, unless otherwise noted, are carried out at atmospheric pressure, room temperature, and in the presence of an air atmosphere.

Preparation of [Ar]-Acetyl Tetrahydrocannabidiol

Tetrahydrocannabidiol (9.6 mg, 0.03 mmole) is dissolved in Acetic Anhydride (1 ml, 10 mmole) and loaded into a stainless-steel pressure vessel. The vessel is heated to 220° C. for one hour. The contents are stirred with 10 ml $H_2O$ at 95 C for 4 hours to hydrolyze excess reagent. Intermediate ester product is isolated by extraction with Hexanes, followed by stripping under vacuum. The intermediate ester product is dissolved in 10 ml 85% Aqueous Ethanol containing Sodium Bicarbonate (250 mg, 3 mmole) and stirred at 60 C for 6 hours. The cooled reaction mixture is acidified with Acetic acid to pH 6, stripped of Ethanol and extracted with Hexanes. The Hexanes extract is stripped under vacuum to yield product (9.5 mg, 0.026 mmole, 87%) as a waxy solid.

Preparation of [Ar]-Butyryl Hexahydrocannibidiol

Tetrahydrocannbidiol (9.54 g, 30 mmole) is dissolved in Butyric Anhydride (50 ml, 300 mmole) and heated at reflux for one hour; by-product butyric acid is distilled and the reaction refluxed one hour at 200 C. Excess Butyric Anhydride is removed under vacuum and the residue stirred with 100 ml H2O at 95 C for 24 hours. Intermediate Ester product is isolated by extraction with Hexanes, followed by stripping under vacuum. The intermediate ester product is dissolved in 500 ml 85% Aqueous Ethanol containing Sodium Bicarbonate (25 g, 300 mmole) and stirred at 65 C for 48 hours. The cooled reaction mixture is acidified with Acetic acid to pH 6, stripped of Ethanol and extracted with Hexanes. The Hexanes extract is stripped under vacuum to yield product (11.3 g, 29.1 mmole, 97%) as an oily solid.

Preparation of [Ar]-Propionyl Tetrahydrocannabidiol

Tetrahydrocannabidiol (64 mg, 0.2 mmole) is dissolved Propionic Anhdyride (1 ml, 7.7 mmoles) and loaded into a stainless steel pressure vessel. The vessel is heated at 220 C for one hour. The contents are stirred with 10 ml H2O at 95 C for 4 hours to hydrolyze excess reagent. Intermediates ester product is isolated by extraction with Hexanes, followed by stripping under vacuum. The intermediate ester product is dissolved in 20 ml 80% Aqueous Ethanol containing Sodium Bicarbonate (0.5 g, 6 mmole) and stirred at 60 C for 24 hours. The cooled reaction mixture is acidified with Acetic Acid to pH6, stripped of Ethanol and extracted with Hexanes. The Hexanes extract is stripped under vacuum to yield product (60 mg, 0.16 mmole, 80%) as a glassy solid.

Preparation of [Ar]-Isobutyryl Tetrahydrocannabidiol

Tetrahydrocannadidiol (9.54 g, 30 mmole) is dissolved in Isobutyric Anhydride (50 ml, 300 mmole) and heated at reflux for one hour; byproduct isobutyric acid is distilled and the reaction refluxed one hour at 200 C. Excess Isobutyric Anhydride is removed under vacuum and the residue stirred with 100 ml H2O at 95 C for 24 hours. Intermediate ester product is isolated by extraction with Hexanes, followed by stripping under vacuum. The intermediate ester product is dissolved in 500 ml 85% Aqueous Ethanol containing Sodium Bicarbonate (25 g, 300 mmole) and stirred at 65 C for 48 hours. The cooled reaction mixture is acidified with 5% Acetic Acid to pH 6, stripped of Ethanol and extracted with Hexanes. The Hexanes extract is stripped under vacuum to yield product (11.1 g, 28.6 mmole, 95%) as a viscous oil.

Preparation of [Ar]-2,2-Dimethylpropionyl Tetrahydrocannibidiol

Tetrahydrocannabidiol (9.54 g, 30 mmole) is dissolved in Pivalic Anhydride (60 ml, 29.6 mmole) and heated at reflux for two hours; by-product pivalic acid was distilled and the reaction refluxed for four hours at 200 C. Excess reagent was removed under vacuum and the residue stirred with 100 ml H2O at 95 C for 24 hours. Intermediate Ester product is obtained by extraction with Hexanes, followed by vacuum stripping. The intermediate ester product is dissolved in 500 ml 90% Aqueous Ethanol containing Potassium Hydroxide (19.8 g, 300 mmole) and stirred at 65 C for 48 hours. The cooled reaction mixture is acidified with 5% Acetic Acid to pH6, stripped of Ethanol, and extracted with Hexanes. The Hexanes extract is washed three times with 100 ml pH5.5 buffer then stripped under vacuum to yield product (11.6 g, 28.8 mmole, 96%) as a hard waxy solid.

Preparation of [Ar]-Benzoyl Tetrahydrocannabidiol

Tetrahydrocannabidiol (0.954 g, 3 mmole) and Benzoic Anhydride (10.2 g, 45 mmoles) were heated to 210 C for six hours. After cooling, the reaction was diluted with 100 ml H2O and refluxed for 24 hours. Intermediate ester was collected by neutralization with aqueous Sodium Bicarbonate solution and extraction with Hexanes, followed by stripping of the Hexanes layer. The intermediate ester product is dissolved in 50 ml 90% Aqueous Ethanol containing Potassium Hydroxide (2.0 g, 30 mmole) and stirred a 65 C for 72 hours. The cooled reaction mixture is acidified with 5% Acetic Acid to pH5.5, stripped of Ethanol, and extracted with Hexanes. The Hexanes extract is washed three times with 100 ml pH5.5 buffer then stripped under vacuum to yield product (1.18 g, 2.88 mmole, 93%) as a crystalline solid.

Preparation of [Ar]-Propionyl Tetrahydrocannabigerol

Tetrahydrocannabigerol (0.96 g, 3 mmole) is dissolved in Propionic Anhydride (15 ml, 117 mmole) and refluxed one hour; by-product propionic acid is distilled and the mixture refluxed at 200 C for 2 hours. Excess Propionic Anhydride is distilled under vacuum and the residue refluxed with 50 ml H2O for 12 hours. The intermediate ester product is isolated by extraction with Hexanes, followed by vacuum stripping. The intermediate ester product is dissolved in 50 ml 85% Aqueous Ethanol containing Sodium Bicarbonate (2.5 g, 30 mmole) and stirred at 65 C for 24 hours. The cooled reaction mixture is neutralized with 5% Acetic Acid to pH 6 and extracted with Hexanes. The Hexanes extract is stripped under vacuum to yield product (1.00 g, 2.66 mmole, 88%) as a greasy solid. Product can be recrystallized from Petroleum Ether to give fine waxy plates.

Preparation of [Ar]-Butyryl Tetrahydrocannabigerol

Tetrahydrocannabigerol (0.96 g, 3 mmole) is dissolved in Butyric Anhydride (15 ml, 95 mmoles) and refluxed for one hour; by-product butyric acid is distilled and the reaction refluxed at 200 C for 3 hours. Excess Butyric Anhydride is removed under vacuum and the residue refluxed with 50 ml H2O for 24 hours. Intermediate ester product is isolated by extraction with Hexanes, followed by vacuum stripping. The intermediate ester product is dissolved in 50 ml 85% Aqueous Ethanol containing Sodium Bicarbonate (2.5 g, 30 mmole) and stirred at 65 C for 24 hours. The cooled reaction mixture is neutralized with 5% Acetic Acid to pH 6 and extracted with Hexanes. The Hexanes extract is stripped under vacuum to yield product (1.09 g, 2.86 mmole, 95%) as a greasy solid. Product can be recrystallized from Petroleum Ether to give fine waxy plates.

Preparation of [Ar]-Benzoyl Tetrahydrocannabigerol

Tetrahydrocannabigerol (0.96 g, 3 mmole) and Benzoic Anhydride (10.2 g, 45 mmoles) were heated to 210 C for six hours. After cooling, the reaction was diluted with 100 ml H2O and refluxed for 24 hours. Intermediate ester was collected by neutralization with aqueous Sodium Bicarbonate solution and extraction with Hexanes, followed by stripping of the Hexanes layer. The intermediate ester product is dissolved in 50 ml 90% Aqueous Ethanol containing Potassium Hydroxide (2.0 g, 30 mmole) and stirred a 65 C for 72 hours. The cooled reaction mixture is acidified with 5% Acetic Acid to pH5.5, stripped of Ethanol, and extracted with Hexanes. The Hexanes extract is washed three times with 100 ml pH 5.5 buffer then stripped under vacuum to yield product (1.20 g, 2.83 mmole, 94%) as a crystalline solid.

While the inventive features have been particularly shown and described with reference to preferred embodiments thereof, it will be understood by those in the art that the foregoing and other changes may be made therein without departing from the sprit and the scope of the disclosure. Likewise, the various diagrams may depict an example architectural or other configuration for the disclosure, which is done to aid in understanding the features and functionality that can be included in the disclosure. The disclosure is not restricted to the illustrated example architectures or configurations but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied alone or in some combination, to one or more of the other embodiments of the disclosure, whether or not such embodiments are described, and whether or not such features are presented as being a part of a described embodiment. Thus, the breadth and scope of the present disclosure should not be limited by any of the above-described exemplary embodiments.

What is claimed is:

1. A compound of Formula I:

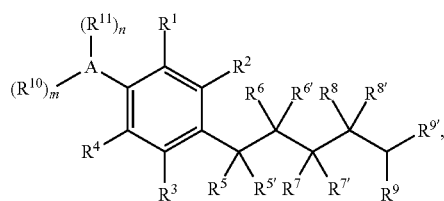

(I)

or a pharmaceutically acceptable salt thereof, wherein:

$R^1$ and $R^4$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, $-OR^{12}$, $-C(=O)R^{12}$, $-C(=O)OR^{12}$, $-OC(=O)R^{12}$, $-OC(=O)OR^{12}$, $-NHC(=O)R^{12}$, $-N(R^{13})(R^{14})$, $-C(=O)N(R^{13})(R^{14})$, $-OC(=O)N(R^{13})(R^{14})$, $-NHC(=O)N(R^{13})(R^{14})$, and $-C(=O)CHR^{15}N(R^{13})(R^{14})$, each of which group may optionally be unsubstituted or substituted with one or more substituents, $R^2$ is independently selected from $-(C_1-C_6)$alkyl, $-C(=O)(C_1-C_6)$alkyl, $-C(=O)O(C_1-C_6)$alkyl, $-CN$, $-C(=O)NH(C_1-C_6)$alkyl, $-C(=O)N[(C_1-C_6)$alkyl$]_2$, $-C(=O)CHR^{15}NH(C_1-C_6)$alkyl, and $-C(=O)CHR^{15}N[(C_1-C_6)$alkyl$]_2$;

$R^3$ is hydrogen; or $R^1$ and $R^2$, and/or $R^2$ and $R^5$, and/or $R^2$ and $R^6$, and/or $R^2$ and $R^7$, taken together with the carbon atoms to which each are attached, independently form a 4- to 8-membered ring, wherein 1 or 2 of the ring atoms independently are optionally replaced by $-O-$, $-(C(=O)-$, $-(C(=O)O-$, $-NH-$, $-N(C_1-C_6$alkyl$)-$, $-(C(=O)NH-$, or $-(C(=O)N(C_1-C_6$alkyl$)-$, and R' and $R^4$ are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, $-C(=O)R^{12}$, $-C(=O)OR^{12}$, $-OC(=O)R^{12}$, $-OC(=O)OR^{12}$, $-NHC(=O)R^{12}$, $-N(R^{13})(R^{14})$, $-C(=O)N(R^{13})(R^{14})$, $-OC(=O)N(R^{13})(R^{14})$, $-NHC(=O)N(R^{13})(R^{14})$, and $-C(=O)CHR^{15}N(R^{13})(R^{14})$, each of which group may optionally be unsubstituted or substituted with one or more substituents;

$R^5$, $R^{5'}$, $R^6$, $R^{6'}$, $R^7$, $R^{7'}$, $R^8$, $R^{8'}$, $R^9$, and $R^{9'}$ are each independently selected from hydrogen, hydroxyl, halogen, alkyl, alkenyl, alkynyl, cycloalkyl, cycloalkenyl, heterocycloallcyl, alkoxy, aryl, aralkyl, heteroaryl, heteroaralkyl, nitro, cyano, $-OR^{12}$, $-C(=O)R^{12}$, $-C(=O)OR^{12}$, $-OC(=O)R^{12}$, $-OC(=O)OR^{12}$, $-NHC(=O)R^{12}$, $-N(R^{13})(R^{14})$, $-C(=O)N(R^{13})(R^{14})$, $-OC(=O)N(R^{13})(R^{14})$, $-NIIC(=O)N(R^{13})(R^{14})$, and $-C(=O)CHR^{15}N(R^{13})(R^{14})$, each of which group may optionally be unsubstituted or substituted with one or more substituents, or $R^5$, $R^{5'}$, and/or $R^6$, $R^{6'}$, and/or $R^7$, $R^{7'}$, and/or $R^8$, $R^{8'}$, and/or $R^9$, and $R^{9'}$ each independently form C=O, C=S, or C=NH, or $R^5$ and $R^6$, or $R^5$ and $R^6$, or $R^6$ and $R^7$, or $R^6$ and $R^8$, or $R^7$ and $R^8$, or $R^7$ and $R^9$, or $R^8$ and $R^9$ taken together with the carbon atoms to which each are attached, independently form a 4- to 8-membered ring, wherein 1 or 2 of the ring atoms independently are optionally replaced by $-O-$, $-(C(=O)-$, $-(C(=O)O-$, $-NH-$, $-N(C_1-C_6$alkyl$)-$, $-(C(=O)NH-$, or $-(C(=O)N(C_1-C_6$alkyl$)-$, and the remainder of $R^5$ and $R^6$, or $R^5$ and $R^7$, or $R^6$ and $R^7$, or $R^6$ and $R^8$, or $R^7$ and $R^8$, or $R^7$ and $R^9$, or $R^8$ and $R^9$, are each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, $-OR''$, $-C(=O)R^{12}$, $-C(=O)OR^{12}$, $-OC(C)R^{12}$, $-OC(=O)OR^{12}$, $-NHC(=O)R^{12}$, $-N(R^{13})(R^{14})$, $-C(=O)N(R^{13})(R^{14})$, $-OC(=O)N(R^{13})(R'')$, $-NHC(=O)N(RD)(R^{14})$, and $-C(=O)CHR^{15}N(R^{13})(R^{14})$, each of which group may optionally be unsubstituted or substituted with one or more substituents;

A is independently selected from alkyl, alkenyl, alkynyl, cycloalkyl, cycloalkenyl, heterocycloalkyl, alkoxy, aryl, aralkyl, heteroaryl, heteroaralkyl, 5- or 6-membered heterocyclic ring, 5- or 6-membered heteroaryl ring, and a 6-membered aryl ring, each of which group may be optionally unsubstituted or substituted with one or more substituents;

$R^{10}$ and $R^{11}$ are each independently selected from hydrogen, hydroxyl, halogen, alkyl, alkenyl, alkynyl, cycloalkyl, spiroalkyl, cycloalkenyl, heterocycloalkyl, alkoxy, aryl, aralkyl, heteroaryl, heteroaralkyl, nitro, cyano, $-OR^{12}$, $-C(=O)R^{12}$, $-C(=O)OR^{12}$, $-OC(=O)R^{12}$, $-OC(=O)OR^{12}$, $-NHC(=O)R^{12}$, $-N(R^{13})(R^{14})$, $-C(=O)N(R^{13})(R^{14})$, $-OC(=O)(R^{13})(R^{14})$, $-NHC(=O)N(R^{13})(R^{14})$, and $-C(=O)CHR^{15}N(R^{13})(R^{14})$, each of which group may optionally be unsubstituted or substituted with one or more substituents, or $R^{10}$ and $R^{11}$, taken together with the atom to which they are attached, independently form a substituted or unsubstituted 4 to 8 membered cyclic or heterocyclic ring, or a 5 membered heteroaryl ring, or a 6 membered aryl ring;

m and n are each independently an integer ranging from 0 to 5;

$R^{12}$ is each independently selected from hydrogen, hydroxyl, halogen, alkyl, alkenyl, alkynyl, cycloalkyl, cycloalkenyl, heterocycloalkyl, alkoxy, aryl, aralkyl, heteroaryl, heteroaralkyl, nitro, cyano, $-N(R^{13})(R^{14})$, $-C(=O)N(R^{13})(R^{14})$, $-OC(=O)N(R^{13})(R^{14})$, $-NHC(=O)N(R^{13})(R^{14})$, and $-C(=O)CHR^{15}N(R^{13})(R^{14})$, each of which group may optionally be unsubstituted or substituted with one or more substituents;

$R^{13}$ and $R^{14}$ are each independently selected from hydrogen, alkyl, alkenyl, alkynyl, cycloalkyl, cycloalkenyl, heterocycloalkyl, aryl, aralkyl, heteroaryl, and heteroaralkyl, or $R^{13}$ and $R^{14}$, taken together with the nitrogen atom to which they are attached, independently form a 4- to 8-membered heterocyclic ring wherein 1 or 2 of the ring atoms independently are optionally replaced by $-O-$, $-S-$, $-S(=O)-$, $-S(=O)_2-$, $-NH-$, $-N(alkyl)-$, $-N(C(=O)R^{12'})-$, or $-N(S(O)_2-R^{12'})-$; and $R^{15}$ is independently selected from hydrogen, alkyl, alkenyl, alkynyl, cycloalkyl, cycloalkenyl, heterocycloalkyl, aryl, aralkyl, heteroaryl, and heteroaralkyl.

2. The compound of claim 1, wherein A has formula:

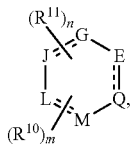

wherein:

Q, E, G, J, L, and M are each independently selected from $-C-$, $-CH-$, $-CR10-$, $-CR11-$, $-C=$, $-N-$, $-NH-$, $-NR10-$ $-NR11-$, $-N=$, $-O-$, and $-S-$, or one of Q, E, G, J, L, and M is and absent, and the other of Q, E, G, J, L, and M are each independently selected from $-C-$, $-CH-$, $-CR10-$, $-CR11-$, $-N-$, $-NH-$, $-NR10-$ $-NR11-$, $-O-$, and $-S-$.

3. The compound of claim 1, wherein $R^1$ and $R^4$ are each independently selected from hydrogen, $-OR^{12}$, and $-N(R^{13})(R^{14})$.

4. The compound of claim 1, wherein $R^1$ and $R^4$ are each independently selected from hydrogen, $-OH$, $-O(C_1-C_6)$alkyl, $-NH(C_1-C_6)$alkyl, and $-N[(C_1-C_6)$alkyl$]_2$.

5. The compound of claim 1, wherein $R^2$ and $R^3$ are each independently selected from alkyl, $-C(O)R^{12}$, $-C(=O)OR^{12}$, $-CN$, $-C(=O)N(R^{13})(R^{14})$, and $-C(=O)CHR^{15}N(R^{13})(R^{14})$.

6. The compound of claim 1, wherein $R^1$ and $R^4$ are each independently selected from $-OH$ and $-O(C_1-C_6)$alkyl; and $R^2$ and $R^3$ are each independently selected from hydrogen and $-C(=O)(C_1-C_6)$alkyl.

7. The compound of claim 1, wherein $R^5$, $R^{5'}$, $R^6$, $R^{6'}$, $R^7$, $R^{7'}$, $R^8$, $R^{8'}$, $R^9$, and $R^{9'}$ are each independently selected from hydrogen, $-(C_1-C_6)$alkyl, F, Cl, Br, I, $-OH$, and $-O(C_1-C_6)$alkyl.

8. The compound of claim 1, wherein $R^{10}$ and $R^{11}$ are each independently selected from hydrogen and $-(C_1-C_6)$alkyl.

9. The compound of claim 1, wherein $R^{10}$ and $R^{11}$ are each independently selected from hydrogen, $-CH_3$, $-CH_2CH_3$, $-CH=CH_2$, $-CH_2CH_2CH_3$, $-CH=CCH_3$, $-CH_2CH=CH_2$, $-C=CHCH_2CH_3$, $-CH_2CH=CHCH_3$, $-CH_2CH_2CH=CH$, $-CH_2CH(CH_3)_2$, $-CH=C(CH_3)_2$, $-CH_2C(=CH_2)(CH_3)$, $-CH(CH_3)CH_2CH_3$, $-C(=CH_2)CH_2CH_3$, and $-CH(CH_3)C=CH_2$.

* * * * *